United States Patent [19]
Ronald et al.

[11] Patent Number: 5,859,339
[45] Date of Patent: Jan. 12, 1999

[54] NUCLEIC ACIDS, FROM ORYZA SATIVA, WHICH ENCODE LEUCINE-RICH REPEAT POLYPEPTIDES AND ENHANCE XANTHOMONAS RESISTANCE IN PLANTS

[75] Inventors: Pamela C. Ronald; Guo-Liang Wang; Wen-Yuang Song, all of Davis, Calif.

[73] Assignee: The Reagents of the University of California, Oakland, Calif.

[21] Appl. No.: 475,891

[22] Filed: Jun. 7, 1995

Related U.S. Application Data

[63] Continuation-in-part of Ser. No. 373,375, Jan. 17, 1995.
[51] Int. Cl.$^6$ ............................. A01H 5/00; C12N 15/82; C12N 15/63; C07H 21/04
[52] U.S. Cl. .................. 800/205; 435/172.3; 435/320.1; 536/23.6; 536/24.1; 800/DIG. 44; 800/DIG. 57
[58] Field of Search .................................. 53/23–6, 24.1; 435/172.3, 320.1; 800/205, DIG. 44, DIG. 57

[56] References Cited

FOREIGN PATENT DOCUMENTS

WO 93/07279  4/1993  WIPO .

OTHER PUBLICATIONS

Ronald, Pamela C., et al. (1992) "Genetic and physical analysis of the rice bacterial blight resistance locus, Xa21", *Mol. Gen. Genet.*, 236:113–120.

Abenes, M.L.P., et al. (1994) "Orientation and integration of the classical and molecular genetic maps of chromosome 11 in rice", *Euphytica*, 76:81–87.

Wang, Guo–Liang, et al. (1995) "Construction of a rice bacterial artificial chromosome library and identification of clones linked to the Xa–21 disease resistance locus", *The Plant Journal*, 7(3):525–533.

Jiang, J., et al. (1995) "Metaphase and interphase fluorescence in situ hybridization mapping of the rice genome with bacterial artificial chromosomes", *Proc. Natl. Acad. Sci USA*, 92 (10):4487–4491.

Song, Wen–Yuan, et al. (1995) "A receptor kinase–like protein encoded by the rice disease resistance gene, Xa21", *Science*, 270:1804–1806.

Johal, Gurmukh S., et al (1992) "Reductase Activity Encoded by the HM1 Disease Resistance Gene in Maize", *Science*, 258:985–987.

Martin, Gregory B., et al. (1993) "Map–Based Cloning of a Protein Kinase Gene Conferring Disease Resistance in Tomato", *Science*, 262:1432–1436.

Bent, Andrew F., et al. (1994) "*RPS2 of Arabidopsis thaliana*: A Leucine–Rich Repeat Class of Plant Disease Resistance Genes", *Science*, 265:1856–1860.

Jones, David A., et al. (1994) "Isolation of the Tomato Cf–9 Gene for Resistance to *Cladosporium fulvum* by Transposon Tagging", *Science*, 266:789–793.

*Primary Examiner*—Douglas W. Robinson
*Assistant Examiner*—Thanda Wai
*Attorney, Agent, or Firm*—Townsend and Townsend and Crew, LLP

[57] ABSTRACT

The present invention provide nucleic acids encoding polypeptides which confer resistance to Xanthomonas spp. The nucleic acids can be used to produce transgenic plants resistant to the pathogen.

24 Claims, 6 Drawing Sheets

NO SmaI, PstI, KpnI IN SalI FRAGMENT pB812

NO XbaI, BamHI, SmaI, KpnI IN XbaI FRAGMENT pB831-pB832

NO SmaI, SalI SITES

```
RICE     pB806   |Sx|xx|xx|xx|x|xx|x|S|x|           23x24
YEAST    adcyc   |xx|xx|xx|xx|x|xx|x|xxL            28x23
FLY      TO11    |xx|FxHxxNLxxLxLxxNxLxxL           30x24
ARAB     RLK5    |xx|xx|xx|xx|x||x|x|S|x|           21x24
SNAP     Fil2    |xx|xx|xx|xS|x||x|x|x|xI           10x24
TOMATO   PGIP    |xxxxx|xx|xx|x||x|x|x|xI           10x24
TOMATO   CF9     |Sx|xx|xx|xx|x||xxx|x|xI           28x24
```

NUCLEIC ACIDS, FROM ORYZA SATIVA, WHICH ENCODE LEUCINE-RICH REPEAT POLYPEPTIDES AND ENHANCE XANTHOMONAS RESISTANCE IN PLANTS

This is a continuation in part of copending U.S. patent application Ser. No. 08/373,375, filed Jan. 17, 1995. This application is incorporated herein by reference.

STATEMENT AS TO RIGHTS TO INVENTIONS MADE UNDER FEDERALLY SPONSORED RESEARCH AND DEVELOPMENT

This invention was made with Government support under Grant No. GM47907, awarded by the National Institutes of Health and Grant No. 9300834, awarded by the United States Department of Agriculture. The Government has certain rights in this invention.

FIELD OF THE INVENTION

The present invention relates generally to plant molecular biology. In particular, it relates to nucleic acids and methods for conferring disease resistance in plants.

BACKGROUND OF THE INVENTION

Loci conferring disease resistance have been identified in many plant species. Genetic analysis of many plant-pathogen interactions has demonstrated that plants contain loci that confer resistance against specific races of a pathogen containing a complementary avirulence gene. Molecular characterization of these genes should provide means for conferring disease resistance to a wide variety of crop plants.

Those plant resistance genes that have been characterized at the molecular level fall into four classes. One gene, Hm1 in corn, encodes a reductase and is effective against the fungal pathogen *Cochliobolus carbonum* (Johal et al. *Science* 258:985–987 (1992)). In tomato, the Pto gene confers resistance against Pseudomonas syringae that express the avrPto avirulence gene Martin et al. *Science* 262:1432 (1993)). The predicted Pto gene product resembles a serine threonine protein kinase. The tomato Cf-9 gene confers resistance to races of the fungus Cladosporium fulvum that carry the avirulence gene Avr9 (Jones et al. *Science* 266:789–793 (1994). Finally, the RPS2 gene of *Arabidopsis thaliana* confers resistance to *P. syringae* that express the avrRpt2 avirulence gene (Bent et al *Science* 265:1856–1860 (1994)).

Bacterial blight disease caused by Xanthomonas spp. infects virtually all crop plants and leads to extensive crop losses worldwide. Bacterial blight disease of rice (*Oryza sativa*), caused by *Xanthomonas oryzae* pv. oryzae (Xoo), is an important disease of this crop. Races of Xoo that induce resistant or susceptible reactions on rice cultivars with distinct resistance (Xa) genes have been identified (Mew 1987). One source of resistance (Xa21) had been identified in the wild species Oryza longistaminata (Khush et al in *Proceedings of the International Workshop on Bacterial Blight of Rice.* (International Rice Research Institute, 1989) and Ikeda et al. Jpn J. *Breed* 40 (Suppl. 1):280–281 (1990)). Xa21 is a dominant resistance locus that confers resistance to all known isolates of Xoo and is the only characterized Xa gene that carries resistance to Xoo race 6. Genetic and physical analysis of the Xa21 locus has identified a number of tightly linked markers on chromosome 11 (Ronald et al. *Mol. Gen. Genet.* 236:113–120 (1992)). The molecular mechanisms by which the Xa21 locus confers resistance to this pathogen were not identified, however.

Considerable effort has been directed toward cloning plant genes conferring resistance to a variety of bacterial, fungal and viral diseases. Only one pest resistance gene has been cloned in monocots. Since monocot crops feed most humans and animals in the world, the identification of disease resistance genes in these plants is particularly important. The present invention addresses these and other needs.

SUMMARY OF THE INVENTION

The present invention provides isolated nucleic acid constructs comprising a Xa21 polynucleotide sequence, which hybridizes to SEQ ID No:1 or to SEQ ID No:3 under stringent conditions. Exemplary Xa21 polynucleotide sequences encode an Xa21 polypeptide as shown in SEQ ID No:2 or SEQ ID No:4. The Xa21 polynucleotide usually encodes a protein having a leucine rich repeat motif and/or a cytoplasmic protein kinase domain. The nucleic acid construct of the invention may further comprise a promoter operably linked to the Xa21 polynucleotide sequence. The promoter may be a tissue-specific promoter or a constitutive promoter.

The invention also provides nucleic acid constructs comprising a promoter sequence from an Xa21 gene linked to a heterologous polynucleotide sequence. Exemplary heterologous polynucleotide sequences include structural genes which confer pathogen resistance on plants.

The invention further provides transgenic plants comprising a recombinant expression cassette comprising a promoter from an Xa21 gene operably linked to a polynucleotide sequence as well as transgenic plants comprising a recombinant expression cassette comprising a plant promoter operably linked to a Xa21 polynucleotide sequence. Although any plant can be used in the invention, rice and tomato plants may be conveniently used.

The invention further provides methods of enhancing resistance to Xanthomonas in a plant. The methods comprise introducing into the plant a recombinant expression cassette comprising a plant promoter operably linked to an Xa21 polynucleotide sequence. The methods may be conveniently carried out with rice or tomato plants.

Definitions

The term "plant" includes whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants.

A "heterologous sequence" is one that originates from a foreign species, or, if from the same species, is substantially modified from its original form. For example, a promoter operably linked to a heterologous structural gene is from a species different from that from which the structural gene was derived, or, if from the same species, one or both are substantially modified from their original form.

An "Xa21 polynucleotide sequence" is a subsequence or full length polynucleotide sequence of an Xa21 gene, such as the rice Xa21 gene, which, when present in a transgenic plant confers resistance to Xanthomonas spp. (e.g., *X. oryzae*) on the plant. Exemplary polynucleotides of the invention include the coding region of SEQ ID No:1 and SEQ ID No:3. An Xa21 polynucleotide is typically at least about 3100 nucleotides to about 6500 nucleotides in length, usually from about 4000 to about 4500 nucleotides.

An "Xa21 polypeptide" is a gene product of an Xa21 polynucleotide sequence, which has the activity of Xa21, i.e., the ability to confer resistance to *Xanthomonas spp.* Xa21 polypeptides are characterized by the presence of an extracellular domain comprising a region of leucine rich repeats (LRR) and/or a cytoplasmic protein kinase domain. Exemplary Xa21 polypeptides of the invention are SEQ ID No:2 and SEQ ID No:4.

Xa-21 genes are members of a new class of disease resistance genes, referred to here as RRK genes, because the encoded polypeptides (RRK polypeptides) comprise an extracellular LLR domain and a cytoplasmic protein kinase domain. Using standard nucleic acid hybridization techniques, one of skill can identify other members of this class of genes. For instance, a nucleic acid probe from an Xa21 gene detected polymorphisms that segregated with the blast (*Pyricularia oryzae*) resistance gene (Pi7) in 58 recombinant inbred lines of rice. The same probe also detected polymorphism in nearly isogenic lines carrying xa5 and Xa10 resistance genes.

In the expression of transgenes one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional Xa21 polypeptide, one of skill will recognize that because of codon degeneracy, a number of polynucleotide sequences will encode the same polypeptide. These variants are specifically covered by the term "Xa21 polynucleotide sequence". In addition, the term specifically includes those full length sequences substantially identical (determined as described below) with an Xa21 gene sequence and that encode proteins that retain the function of the Xa21 protein. Thus, in the case of rice Xa21 genes disclosed here, the above term includes variant polynucleotide sequences which have substantial identity with the sequences disclosed here and which encode proteins capable of conferring resistance to Xanthomonas on a transgenic plant comprising the sequence.

Two polynucleotides or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a segment or "comparison window" to identify and compare local regions of sequence similarity. The segment used for purposes of comparison may be at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95%, compared to a reference sequence using the programs described above (preferably BESTFIT) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other under stringent conditions. Stringent conditions are sequence dependent and will be different in different circumstances. Generally, stringent conditions are selected to be about 5° C. to about 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code.

As used herein, a homolog of a particular Xa21 gene (e.g., the rice Xa21 genes disclosed here) is a second gene (either in the same species or in a different species) which has a polynucleotide sequence of at least 50 contiguous nucleotides which are substantially identical (determined as described above) to a sequence in the first gene. It is believed that, in general, homologs share a common evolutionary past.

BRIEF DESCRIPTION OF THE DRAWINGS

FIG. 2 shows a comparison of the leucine rich repeats of a protein of the invention (SEQ ID No:5) and proteins from yeast (SEQ ID No:6), Drosophila (SEQ ID No: 7), Arabidopsis (SEQ ID No:8), snapdragon (SEQ ID No:9), and tomato (PGIP, SEQ ID NO:10 and Cf-9, SEQ ID NO:11).

DESCRIPTION OF THE PREFERRED EMBODIMENTS

Figure 1A:
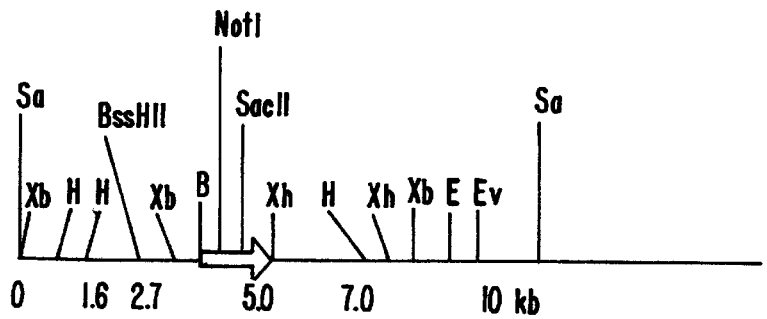
FIGS. 1A–F show partial restriction maps of BAC and cosmid clones containing regions that hybridized to Xa21-specific probes.
Figure 1B:
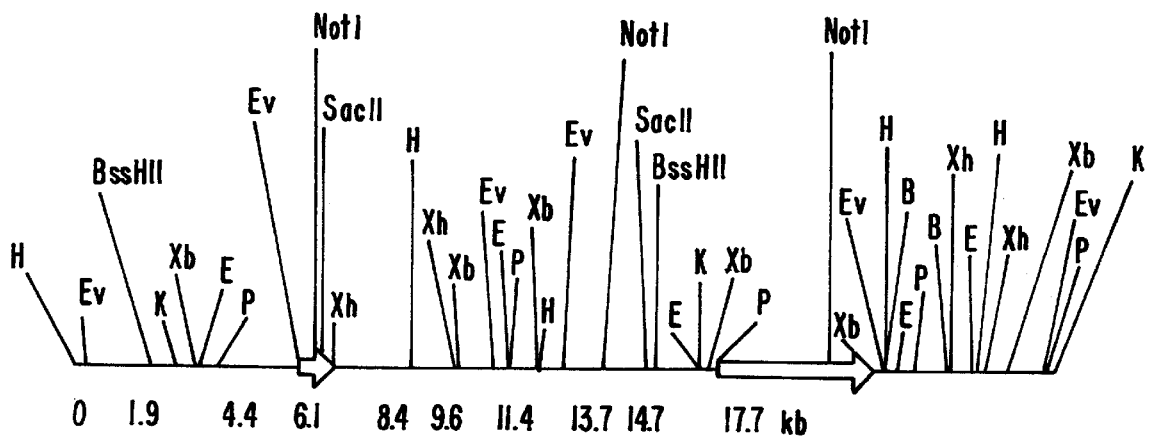
Figure 1C:
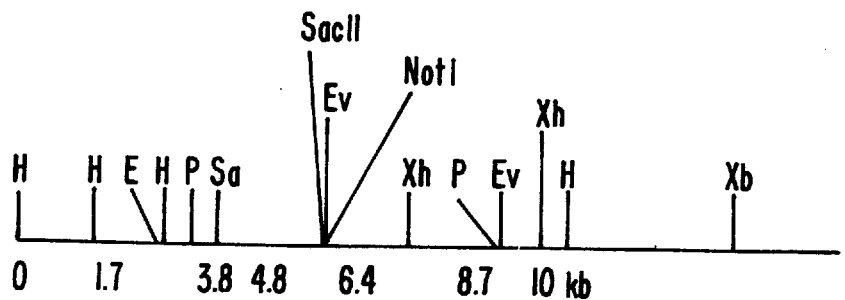
Figure 1D:
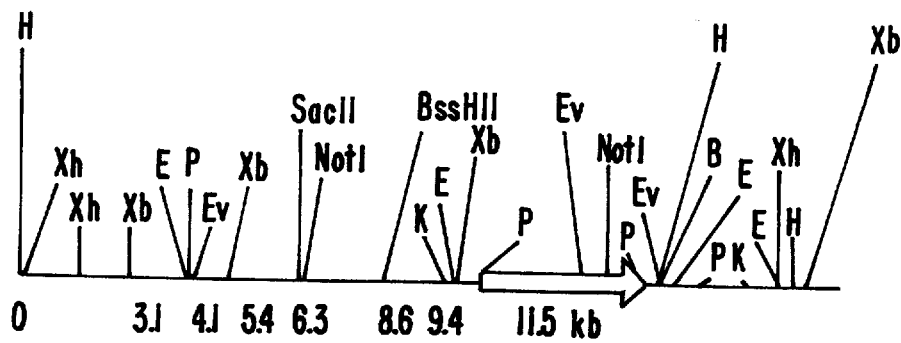
Figure 1E:
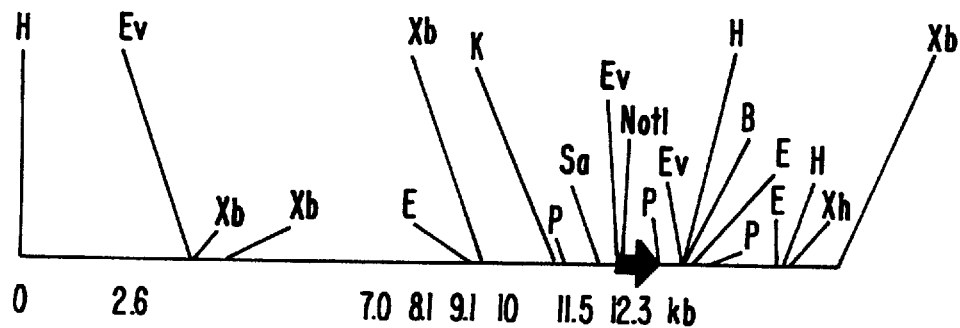

This invention relates to plant Xa21 genes. Nucleic acid sequences from Xa21 genes can be used to confer resistance to Xanthomonas and other pathogens in plants. The invention has use in conferring resistance in all higher plants susceptible to pathogen infection. The invention thus has use over a broad range of types of plants, including species from the genera Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Zea, Avena, Hordeum, Secale, Triticum, and, Sorghum.

The Example section below, which describes the isolation and characterization of Xa21 genes in rice, is exemplary of a general approach for isolating Xa21 genes. The isolated genes can then be used to construct recombinant vectors for transferring Xa21 gene expression to transgenic plants.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual,* Cold Spring Harbor Laboratory, Cold Spring Harbor, N.Y., (1989).

The isolation of Xa21 and related genes may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as leaf and a cDNA library which contains the Xa21 gene transcript is prepared from the mRNA. Alternatively, cDNA may be prepared from mRNA extracted from other tissues in which Xa21 genes or homologs are expressed.

The cDNA or genomic library can then be screened using a probe based upon the sequence of a cloned Xa21 gene such as rice Xa21 genes disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology to amplify the sequences of the Xa21 and related genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying Xa21 sequences from plant tissues are generated from comparisons of the sequences provided herein. For a general overview of PCR see *PCR Protocols: A Guide to Methods and Applications.* (Innis, M, Gelfand, D., Sninsky, J. and White, T., eds.), Academic Press, San Diego (1990), incorporated herein by reference.

Polynucleotides may also be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Isolated sequences prepared as described herein can then be used to provide Xa21 gene expression and therefore Xanthomonas resistance in desired plants. One of skill will recognize that the nucleic acid encoding a functional Xa21 protein (e.g., SEQ ID No:2 and SEQ ID No:4) need not have a sequence identical to the exemplified gene disclosed here. In addition, the polypeptides encoded by the Xa21 genes, like other proteins, have different domains which perform different functions. Thus, the Xa21 gene sequences need not be full length, so long as the desired functional domain of the protein is expressed. As explained in detail below, the proteins of the invention comprise an extracellular leucine rich repeat domain, as well as an intracellular kinase domain. Modified protein chains can also be readily designed utilizing various recombinant DNA techniques well known to those skilled in the art. For example, the chains can vary from the naturally occurring sequence at the primary structure level by amino acid substitutions, additions, deletions, and the like. Modification can also include swapping domains from the proteins of the invention with related domains from other pest resistance genes. For example, the extra cellular domain (including the leucine rich repeat region) of the proteins of the invention can be replaced by that of the tomato C-9 gene and thus provide resistance to fungal pathogens of rice. These modifications can be used in a number of combinations to produce the final modified protein chain.

To use isolated Xa21 sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988).

A DNA sequence coding for the desired Xa21 polypeptide, for example a cDNA or a genomic sequence encoding a full length protein, will be used to construct a recombinant expression cassette which can be introduced into the desired plant. An expression cassette will typically comprise the Xa21 polynucleotide operably linked to transcriptional and translational initiation regulatory sequences which will direct the transcription of the sequence from the Xa21 gene in the intended tissues of the transformed plant.

For example, a plant promoter fragment may be employed which will direct expression of the Xa21 in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens,* and other transcription initiation regions from various plant genes known to those of skill.

Alternatively, the plant promoter may direct expression of the Xa21 gene in a specific tissue or may be otherwise under more precise environmental or developmental control. Such promoters are referred to here as "inducible" promoters. Examples of environmental conditions that may effect transcription by inducible promoters include pathogen attack, anaerobic conditions, or the presence of light.

Examples of promoters under developmental control include promoters that initiate transcription only in certain tissues, such as leaves, roots, fruit, seeds, or flowers. The operation of a promoter may also vary depending on its location in the genome. Thus, an inducible promoter may become fully or partially constitutive in certain locations.

The endogenous promoters from the Xa21 genes of the invention can be used to direct expression of the genes. These promoters can also be used to direct expression of heterologous structural genes. Thus, the promoters can be used in recombinant expression cassettes to drive expression of genes conferring resistance to any number of pathogens, including fungi, bacteria, and the like.

To identify the promoters, the 5' portions of the clones described here are analyzed for sequences characteristic of promoter sequences. For instance, promoter sequence elements include the TATA box consensus sequence (TATAAT), which is usually 20 to 30 base pairs upstream of the transcription start site. In plants, further upstream from the TATA box, at positions −80 to −100, there is typically a promoter element with a series of adenines surrounding the trinucleotide G (or T) N G. J. Messing et al., in *Genetic Engineering in Plants,* pp. 221–227 (Kosage, Meredith and Hollaender, eds. 1983).

If proper polypeptide expression is desired, a polyadenylation region at the 3'-end of the Xa21 coding region should be included. The polyadenylation region can be derived from the natural gene, from a variety of other plant genes, or from T-DNA.

The vector comprising the sequences from an Xa21 gene will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

Such DNA constructs may be introduced into the genome of the desired plant host by a variety of conventional techniques. For example, the DNA construct may be introduced directly into the genomic DNA of the plant cell using techniques such as electroporation, PEG poration, particle bombardment and microinjection of plant cell protoplasts or embryogenic callus, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987). Using a number of approaches, cereal species such as rye (de la Pena et al., *Nature* 325:274–276 (1987)), corn (Rhodes et al., *Science* 240:204–207 (1988)), and rice (Shimamoto et al, *Nature* 338:274–276 (1989) by electroporation; Li et al. *Plant Cell Rep.* 12:250–255 (1993) by ballistic techniques) can be transformed.

*Agrobacterium tumefaciens*—meditated transformation techniques are well described in the scientific literature. See, for example Horsch et al. *Science* 233:496–498 (1984), and Fraley et al. *Proc. Natl. Acad. Sci. USA* 80:4803 (1983). Although Agrobacterium is useful primarily in dicots, certain monocots can be transformed by Agrobacterium. For instance, Agrobacterium transformation of rice is described by Hiei et al, *Plant J.* 6:271–282 (1994).

Transformed plant cells which are derived by any of the above transformation techniques can be cultured to regenerate a whole plant which possesses the transformed genotype and thus the desired Xa21-controlled phenotype. Such regeneration techniques rely on manipulation of certain phytohormones in a tissue culture growth medium, typically relying on a biocide and/or herbicide marker which has been introduced together with the Xa21 nucleotide sequences. Plant regeneration from cultured protoplasts is described in Evans et al., *Protoplasts Isolation and Culture, Handbook of Plant Cell Culture,* pp. 124–176, MacMillilan Publishing Company, New York, 1983; and Binding, *Regeneration of Plants, Plant Protoplasts,* pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The methods of the present invention are particularly useful for incorporating the Xa21 polynucleotides into transformed plants in ways and under circumstances which are not found naturally. In particular, the Xa21 polypeptides may be expressed at times or in quantities which are not characteristic of natural plants.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The effect of the modification of Xa21 gene expression can be measured by detection of increases or decreases in mRNA levels using, for instance, Northern blots. In addition, the phenotypic effects of gene expression can be detected by measuring lesion length as in plants. Suitable assays for determining resistance are described below.

The following Examples are offered by way of illustration, not limitation.

EXAMPLE 1

Plant genes may also be isolated using map-based cloning methods. This strategy consists of identifying DNA markers that are tightly linked to the gene or genes of interest. One requirement for the success of map-based cloning and physical analysis of large chromosomal regions is the availability of libraries containing large inserts of genomic DNA. Recently, Shizuya, H., et al., *Proc. Natl. Acad. Sci.* 89, 8794–8797 (1992), described a bacterial artificial chromosome (BAC) system to clone large DNA fragments of the human genome. This system utilizes an F-factor-based vector and is capable of maintaining human genomic DNA fragments of >300 kb. DNA can be cloned with high efficiency, manipulated easily and stably maintained in E. coli. The following is a description of the use of this technique to isolate genes of the invention.

Isolation of BAC and Cosmid Clones Carrying Xa21-Related Sequences BAC Clones

A. Materials and Methods
Preparation of High Molecular Weight DNA in Rice

An International Rice Research Institute (IRRI) rice line, IR-BB21 carrying Xa-21 was used as the plant material. The plants were grown in the greenhouse for 3–5 weeks. Leaf tissue was harvested and washed with distilled water before grinding. High molecular weight DNA was extracted from rice tissue essentially as described by Hatano, S., et al., *Plant Sciences*, 83, 55–64, (1992) and Zhang, H. B., et al., *Plant J.* 7:175–184 (1994), with the following modifications: approximately 20 grams of leaf tissue was ground into powder using a cold mortar and pestle in liquid nitrogen. The powder was suspended by stirring in 200 ml cold nuclei-extraction (NE) buffer (1 MM spermidine, 1 mM spermine, 10 mM $Na_2$ EDTA, 10 mm Trizma base, 80 mM KCl, 0.5% Triton-X 100 and 0.4M sucrose, pH 9.4). The mixture was filtered through two layers of cheesecloth into a GSA bottle and centrifuged at 1200 g at 4° C. for 20 min. The supernatant was poured off and the nuclear pellet (pale green) was resuspended in 50 ml cold NE Buffer. The resuspended pellet was then filtered through an 80-micron sieve into a 50 ml tube to remove green tissue debris and then centrifuged at 1000 g for 10 min. The pellet was resuspended and centrifuged as above without passing through the 80-micron sieves. The nuclear pellet (about $5 \times 10^8$ nuclei/ml) was resuspended in 2.5 ml of SCE buffer (1M sorbitol, 0.1M NaCitrate, 60 mM EDTA, pH 7.0) and embedded in 2.5 ml 1% low-melting-point (LMP) agarose (Ultrapure). 80 μl plugs were incubated in 25 ml ESP solution (0.5M EDTA, pH 9.3, 1% sodium laurel sarcosine, 5 mg/ml proteinase K, Boehringer Mannheim) at 50° C. for two days with one change of the buffer. Each plug contained about 5 μg DNA.
Partial Digestion of High Molecular Weight DNA and Size Fraction by PFGE Agarose plugs were dialyzed twice against TE (10 mm Tris-HCl and 1 mM EDTA, pH 8.0) plus 1 mm PMSF (phenylmethyl sulphonyl fluoride) at 50° C. for one h, and then equilibrated with HindIII buffer (50 mM NaCl, 10 mM Tris-HCl, 10 mM $MgCl_2$ and 1 mM dithiothreitol, pH 7.9) twice at room temperature for one hr. Plugs were melted at 65° C. for 15 min and kept at 37° C. for 5 min before partial digestion. Five to seven units of HindIII (NEB, USA) per plug were added to the DNA solution and incubated at 37° C. for 30 min. The reaction was stopped by addition of 1/10 volume of 0.5M EDTA, pH 8.0. Partially digested DNA was immediately loaded into a 0.8% LMP agarose gel with a pipette tip cut off to an inside diameter of 2 mm and separated by PFGE (CHEF DR II system, BioRad, USA). Two different PFGE methods were used for the library construction. Firstly, the gel was subjected to electrophoresis at 150 V, using an 8 s initial and 8 s final switch time for 16 h at 14° C. The unresolved DNA ($\geq 200$ kb) was focused into a thin band. Secondly, the gel was subject to electrophoresis at 150V, ramped switching time from 60 to 90 s for 16 h at 14° C. For both methods, the gel containing the partially digested DNA was cut and soaked in TE while the marker lanes of the gel were stained with ethidium bromide. The agarose slice containing fragments larger than 200 kb (the first PFGE method) or agarose slice containing 250–350 kb (the second method) was excised from the gel. The agarose slice was equilibrated in TE for 2 h at 4° C., placed in a 1.5 ml tube, melted at 65° C. for 10 min, digested with Gelase (Epicentre, USA) (one unit of enzyme per 100 mg agarose) and incubated at 45° C. for one hr. The DNA solution was directly used for the ligation reaction.
Isolation and Preparation of Vector, and Ligation Reaction The vector, pBeloBAC II, was provided by Drs. H. Shizuya and M. Simon (California Institute of Technology, USA). This vector contains the lacz gene inserted into the vector pBAC108L. Shizuya, et al. (1992). A single colony was inoculated into 5 ml LB media containing 12.5 μg/ml chloramphenicol and grown at 37° C. for 4–5 h before adding to 6 liters of LB media. The inoculum was grown for about 16 h at 37° C. to an $OD_{600nm}$ 1.3–1.5. The plasmid was isolated using Qiagen's plasmid maxi isolation kit (Qiagen, USA). Vector DNA was further purified by cesium chloride/ethidium bromide equilibrium centrifugation at 45,000 RPM for 60 h. The rotor was decelerated to 35,000 RPM for one hr. to allow the gradient to relax, using a fixed anger rotor 70.1 (Beckman, USA). The plasmid was digested with HindIII to completion and assayed by gel electrophoresis. Vector ends were dephosphorylated with HK phosphatase (Epicenter, USA) at 30° C. for one hr., using 1 unit of the enzyme per 1 μg of vector ]DNA. The HK phosphatase was inactivated by heating at 65° C. for 30 min. The ligation was carried out in a 100 μl volume in which about 40 ng of the size-selected rice DNA (about 85 μl) was ligated to 10 ng of HindIII-digested vector (1 μl) molar ratio of about 10 to 1 in vector excess) with 400 units of T4 DNA ligase (NEB, USA) at 16° C. overnight. Before transformation, the litigation was dialyzed against TE in an ULTRAFREE-MC filter tube (Millipore, USA) at 4° C. overnight.
BAC Transformation Transformation of competent *E. coli* DH10B cells (GIBCOBRL, USA) was carried out by electroporation using a Cell-Porator (GIBCO-BRL, USA) at the following settings: voltage: 400; charge rate: fast; voltage booster resistance: 4,000; capacitance: 330μ; impedance: low. Thirteen μl of competent cells were mixed with 0.5–1.0 μl of ligation solution for each electroporation. After electroporation, cells were transferred to 1 ml SOC solution (2% Bacto tryptone, 0.5% Bacto yeast extract, 10 MM NaCl, 2.5 mM KCl, 10 mM $MgCl_2$, 10 mM $MgSO_4$, 20 mM Glucose, pH 7.0) and incubated at 37° C. with gentle shaking (90–95 RPM,) for 45 min. The cells were spread on LB plates containing chloramphenicol (12.5 μg/ml), X-gal (40 μg/ml) and IPTG (isopropylthio-β-D-galactoside) (0.072 μg/ml). Plates were incubated at 37° C. for 24 h. White colonies containing rice DNA inserts were picked to a new LB plate for a second color screen. The BAC clones were transferred to 384-well microtiter plates (Genetix, UK) containing 60 μl of LB freezing buffer (36 mM $K_2HPO_4$, 13.2 mM $KH_2PO_4$, 1.7 mM Citrate, 0.4 MM $MgSO_4$, 6.8 mM $(NH_4)_2SO_4$, 4.4% v/v Glycerol, 12.5 μg/ml chloramphenicol, LB) and incubated at 37° C. for 24 h. Since more than 95% of the colonies were still white on the second screen, only one screen was used in the subsequent experiments, and white colonies were directly picked to 384-well microtiter plates. The library was replicated in duplicate and stored in two different –80° C. freezers.

Filter Preparation

The BAC clones in each 384-well microtiter plate were replicated onto a Hybond $N^+$ filter (Amersham, USA). The filter was put into a plastic box containing LB/agar with 12.5 μg/ml chloramphenicol and the box was kept at 37° C. overnight until the colonies were about 2–3 mm in diameter. Treatment of the filters was as described. Nizetic, D., et al., *Nucl. Acids Res.* 19, 182 (1990); Hoheisel, J. D., et al., *Cell,* 73, 109–120 (1993). Hybridization and washing conditions were the same as described in Hoheisel, et al. (1993). Probes were labeled using random primer extension. Feinberg, A. P. and Vogelstein, B., *Anal Biochem.* 132, 6–13 (1983); Addendum 137, 266–267 (1984).

B. Results

The BAC library described above of consists of 11,000 clones. The library was constructed using two different approaches. A first half of the library having 7269 BAC clones was made with one size selection using a compression zone method as described in Ramsay, M. and Wicking, C., *Protocols in Human Molecular Genetics,* 197–221 (1991). A second half of the library having 3731 clones was made using double size-selection of partially digested DNA. Double size-selection failed, however, to increase the average DNA insert size. Apparently, there were small DNA molecules still present in the size-selected DNA solution (only 250–350 kb DNA isolated). Subsequent experiments demonstrated that double size-selection of DNA between 350–500 kb for ligation yielded larger average insert size in BAC clones. Out of 54 random BAC clones chosen from the library, 50 clones contained rice DNA (93.0%). Some of the clones (7%) contained no inserts. The DNA insert sizes ranged between 30–250 kb with an average of 125 kb.

High molecular weight DNA used to construct the BAC library was isolated from purified rice nuclei. Most of the chloroplasts and mitochondria were removed by low speed centrifugation (<1000 g). The low frequency of chloroplast or mitochondrial clones found in the inventive BAC library (<0.3%) reduces the possibility of organellar/nuclear DNA co-ligation.

The BAC library was used to construct a contiguous set of clones (contig) spanning the Xa21 locus. Two Xa21-linked DNA markers, RG103 (1 kb, see, Ronald, et al. *Mol. Gen. Genet.* 236:113–120 (1992)) and pTA818 (1.2 kb, equivalent to RAPD818 in Ronald, et al) were used to screen the BAC library. RG103 is found in 8 copies in the Xa21-containing line and hybridizes with 8 genomic HindIII DNA fragments in this line. All of these fragments are genetically and physically linked to the Xa21 disease resistance locus. pTA818 hybridizes with 2 DNA fragments and at least one of these fragments is linked to the Xa21 locus. Ronald, et al. (1992).

7296 BAC clones were probed-with pTA818 (2 copies) and RG103 (8 copies). Seven and five BAC clones hybridizing with RG103 and pTA818, respectively, were identified. BAC DNA was isolated from these clones and digested with HindIII. The DNA fragments were separated by PFGE. Southern analysis showed that the 7 RG103 hybridizing BAC clones carried 4 different copies of the RG103 genomic HindIII fragments. The probe was hybridized with a 4.3 kb DNA fragment and 9.5 kb fragment, a 9.6 kb fragment and a 6.2 kb fragment. The size of the DNA fragments are deduced from lambda DNA digested with HindIII.

Four BAC clones were isolated that carried one copy of the pTA818 HindIII fragment and one BAC clone was identified that contained the other copy. One of the pTA818 containing BACs also hybridized with the marker PTA248 (equivalent to RAPD248 in Ronald, et al. (1992), confirming that these two cloned RAPD markers are within 60 kb of each other. Ronald, et al. (1992).

The identification of 12 BAC clones hybridizing with 2 cloned DNA sequences (corresponding to 10 DNA fragments in the rice genome) is slightly lower than the 20 clones expected based on screening 2×genome equivalents (7296 clones, 450,000 kb genome, 125 kb average insert size). Specifically, the pTA818 sequences and four (out of eight) of the RG103 hybridizing sequences are over represented in this portion of the library. By contrast, the other four RG103 hybridizing sequences are under represented. The DNA insert sizes of these clones ranged from 40 to 140 kb.

Cosmid Clones

A. MATERIALS AND METHODS

Preparation of High Molecular Weight (HMW) DNA from Rice Leaves.

The rice line, 1188 carrying the Xa-21 locus, was used as the plant material for isolation of HMW DNA. 120 g 4–6 weeks old leaf tissue was harvested and ground into fine powder using a cold mortar and pestle in liquid nitrogen. The powder was then suspended by stirring in 800 ml cold H buffer [4 mM spermidine, 1 mM spermine, 10 mM EDTA, 10 mM Tris-HCl, 80 mM KCl, 0.5 M sucrose, 1 mM PMSF (phenylmethyl sulphony fluoride, add just before use), 0.5 % (v/v) Triton-X 100, 1/1000 (v/v) β-mercaptoethanol (add just before use), pH 9.5]. The mixture was filtered through an 80-micron sieve into GSA bottles and the pellet resuspended in 400 ml H buffer and filtered again. The two filtrate volumes were combined and centrifuged at 3500 rpm for 10 min at 4° C. The pellet was resuspended in 300 ml washing buffer (same as H buffer except PMSF and β-mercaptoethanol) and centrifuged at 3500 rpm for 10 min at 4° C. The pellet was washed two additional times until the color of the pellet was pale green. The pellet was resuspended in 40 ml washing solution and the nuclei were lysed by adding an equal volume of lysis buffer ( 2% Na laurel sarcosine, 100 mM Tris-HCl, 0.5 M EDTA, pH 9.5) containing 2 mg/ml proteinase K (Boehringer Mannheim). Proteins were removed by incubation at 50° C. for 5 hr and then extraction of the solution (by gentle inversion) with an equal volume of phenol-chloroform-isoamyl alcohol (24:24:1) for 30 min at room temperature. The HMW DNA was precipitated by gently layering ⅒ vol. of 3M sodium acetate (pH 5.5), 2 vol. of ethanol and inverting several times. Finally, the DNA was removed from the ethanol using wide-mouth pipette tips, washed with 70% ethanol, dried and dissolved into 1 ml of TE (10 mM Tris-HCl, 1 mM EDTA, pH8.0) at 4° C. overnight without shaking. Normally, 250 ug HMW DNA can be isolated from 120 g leaves.

Preparation of Insertion DNA
(A) Partial Digestion of HMW DNA

Pilot experiment. 30 ug (70 ul) of HMW DNA was mixed with 10 ul of 10×Sau3AI buffer (NEB) and pre-warmed at 37° C. for 5 min. 20 ul (2 units) of Sau3AI was then added to the DNA solution, gently mixed with a wide-mouth pipette tip and incubated at 37° C. 15 ul aliquots were removed at 0, 5, 10, 20, 30 and 70 min and immediately mixed with 5 ul 0.5M EDTA (pH8.0) on ice to stop the reaction. The samples were analyzed by electrophoresis through a 0.3% agarose/TBE gel at 2 V/cm gel length for 36 hr in the cold room.

Large-scale partial DNA digestion was achieved by repetition of the pilot experiment using the optimized incubation time intervals of 20 min at 37° C.

(B) Size-Selection

The partially digested DNA was fractionated on a sucrose density gradient of 5 to 40% by centrifuge in an SW27 rotor at 26,000 rpm at 20° C. for 13 hr. 0.8 ml fractions (20 total) were collected by carefully placing a capillary tube at the bottom of the centrifuge tube and pumping out the gradient at a very slow speed. 20 ul of each samples was assayed on a 0.3% agarose gel at 2 V/cm gel length for 36 hr. DNA fractions with approximately 35–50 kb were pooled together. After diluting the sucrose with an equal vol. of H2O, the DNA was precipitated with 2 vol. ethanol. The partial fill in reaction was achieved using standard protocols.

Ligation, Packaging and Transfection

The cosmid vector, pHC80, was kindly provided by Dr. Scot Hulbert. Vector and insert DNA were ligated in a 2 to 1 molar ratio, at a final concentration of 0.8 ug/ul. The ligation reaction was carried out with 600 units of T4 DNA ligase (NEB, USA) at 16° C. for overnight. The ligated DNA was in vitro packaged with GigapackII packaging extract (Stratagene, USA) and transfected into competent cell, E.coli NM554, according to the Stratagene manual.

Library Screening 61440 cosmid colonies (more than five genome equivalents) in 160 384-well microtiter plates were transferred onto Hybond N+filters (Amersham, USA) in two type densities. In the first method, the cosmid clones were replicated in low density (1536 colonies/11.5×15 cm filter) using manual replicators (Genetix, U.K.) and grown on LB/agar with 100 ug/ml ampicillin for overnight. Forty filters were made to cover the whole cosmid library. In the second method, the cosmid clones were replicated in high density arrays using a Beckman Biomek™ robotic workstation and grown using the same method as above. Using 3×3 arrays, 3456 colonies were transferred onto an 8.5×12 cm filter. In order to exactly localize the positive colonies on a negative background, a reference cosmid colony (containing the RG103 marker) was plated in the first position of each 3×3 grid. The remaining eight offset position were plated with colonies from eight microtiter plates of the cosmid library. In this case, 20 filters in size of 8.5×12 cm each can cover the whole library. For hybridizations with a unique probe, the RG103 probe was mixed with the unique probe in a ratio of 1:4 to produce the reference pattern.

Bacteria on the filters were lysed and fixed using the steaming water bath procedure with the following modification: colonies were placed face up on top of two pieces of 3 MM Whatman soaked in lysis solution (0.5M NaOH, 1.5M NaCl) for 4 min at room temperature, the plastic boxes containing the filters were incubated in a steaming water bath at 85° C. for 6 min and then the filters were transferred to 3 MM Whatman soaked in neutralization buffer (1M Tris-HCl (pH7.4), 1.5M NaCl) for 4 min. Proteins and cell debris were removed by submergence in 50 ml proteinase K solution (50 mM Tris-HCl (pH8.5), 50 mM EDTA (pH8.0), 100 mM NaCl, 1% (w/v) Na-lauryl-sarcosine, 250 ug/ml proteinase K) and incubated at 37° C. for 20 min. The filters were gently washed in 2×SSC solution for 5 min at room temperature, dried and UV treated the filters at 10 cm for 2.5 min.

Hybridization was performed according to standard procedures as follows: filters were subjected to prehybridization solution (7% SDS, 0.5M $Na_2PO_4$ (pH 7.2), 1 mM EDTA, 100 ug/ml ssDNA) at 65° C. for 2 hr to overnight. Probes were labeled using the random primer extension procedure and hybridization was performed at 65° C. with shaking overnight. The filters were washed briefly in (40 mM $Na_2PO_4$ (pH 7.2), 0.1% SDS) at room temperature and the filters were incubated in the same solution at 65° C. for 20 min with gentle shaking.

B. Results

Three Xa21-linked markers (RG103, RAPD 248 and RAPD 818) were used to screen the cosmid library. Genomic Southern analysis showed that the copy numbers of these three markers in resistant lines are 8, 1 and 2 respectively (unpublished results). Six positive cosmid clones hybridizing with the RG103 marker were identified and confirmed by further Southern analysis. However, no positive clones were identified to contain RAPD248 and RAPD818.

EXAMPLE 2

Characterization of the Xa21 Genes

Figure 1F:
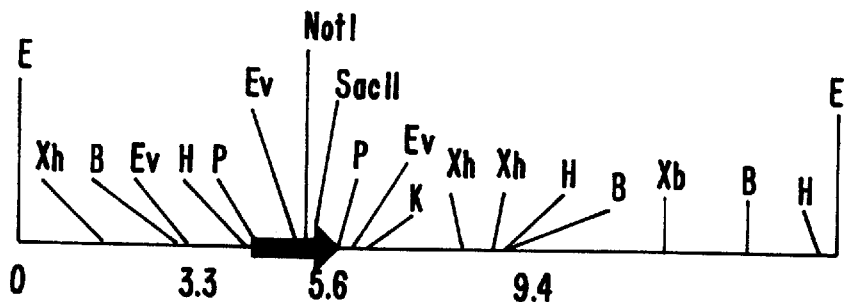

Five cosmid clones and 1 BAC clone isolated in Example 1 were further characterized by restriction enzyme mapping. FIGS. 1A–1E are partial restriction maps of the cosmid clones. FIG. 1F is a partial restriction map of the BAC clone.

An open reading frame in one of the clones, pB806, was identified (SEQ ID No:1). It includes the promoter region, the predicted intron and a partial 3' sequence. SEQ ID No:2 shows the predicted amino acid sequence. The predicted intron has been spliced out.

The predicted amino acid sequence has revealed two features of the protein which indicate it is encoded by a member of the new class of plant disease resistance genes referred to here as RRK genes. First, the extracellular domain of the proteins encoded by these genes comprise a block of about 23 tandem leucine-rich repeats (LRR) with an average length of 24 amino acids (see, FIG. 2). The LRR motif has been implicated in protein-protein interactions and ligand binding in a variety of proteins. The extracellular domain also comprises a region between the LRRs and the signal peptide which contain a motif, SWNTS (SEQ ID No:12), which is conserved among a number of proteins, including, Cf-9, PGIP, and RLK5. In addition, the protein comprises a region with high sequence identity to receptor-like protein kinases (RLPKs) such as RLK5 and TMK1 (Walker et al. *Plant J.* 3:451 (1993); Chang et al. *Plant Cell* 4:1263 (1992); Valon et al. *Plant Molec. Biol.* 23:415 (1993)) as well as the tomato resistance gene product, Pto (Martin et al *Science* 262:1432 (1993). The signal domain, the extracellular domain (including the LRR region), the transmembrane domain and the cytoplasmic kinase domain are identified in SEQ ID No:2.

Figure 3:
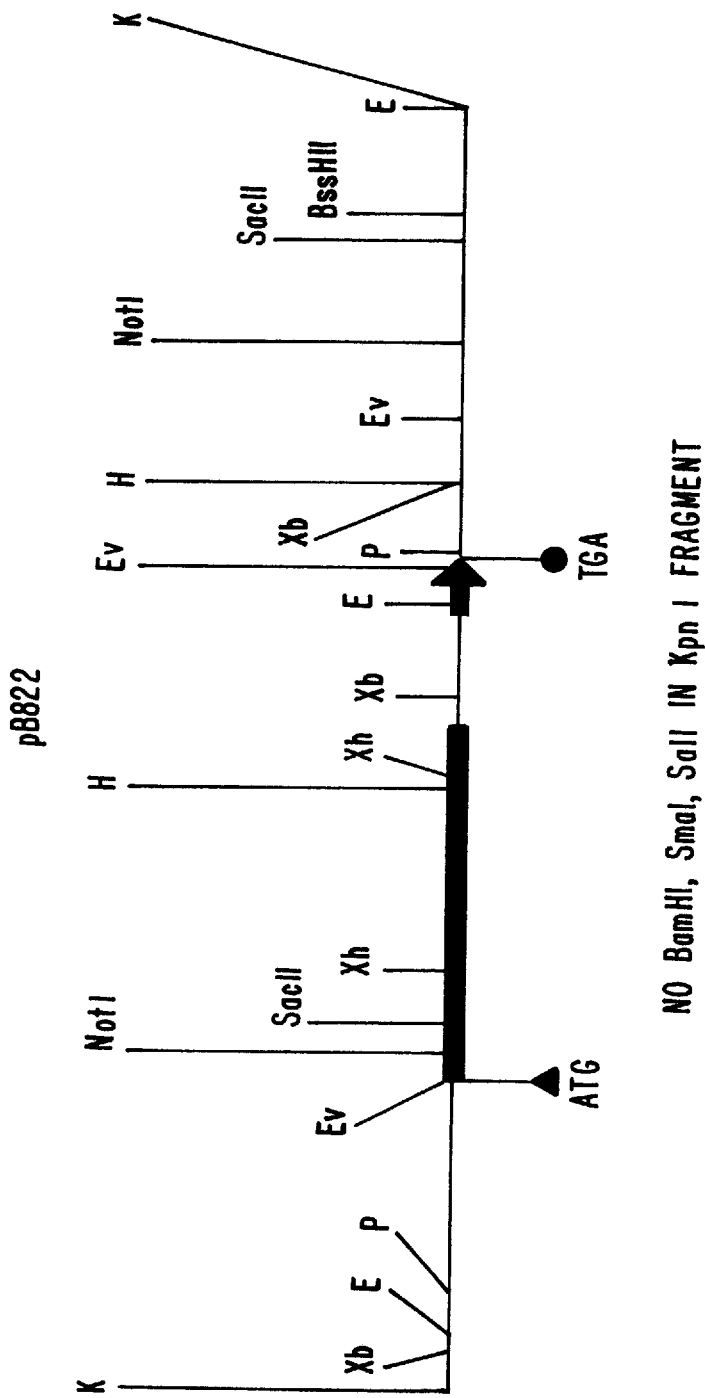
FIG. 3 shows a restriction map of pB822, the most active copy.
Figure 4:
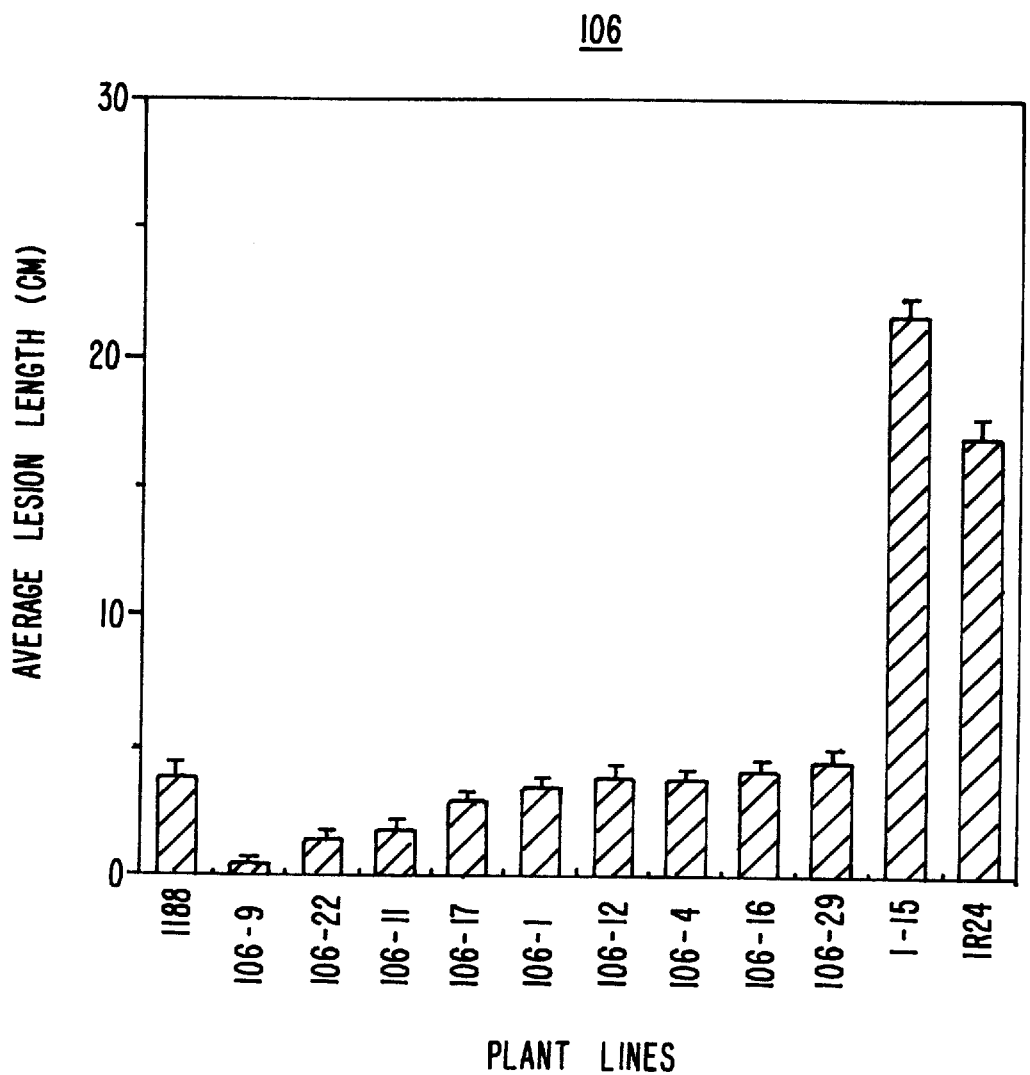
FIG. 4 shows the results of assays measuring Xanthomonas resistance in transgenic plants comprising the Xa21 gene from the pB822 clone.

FIG. 3 is a restriction map of a second clone, pB822, which was used to construct the plasmid used in the transformation experiments described in Example 3, below. The Xa21 gene in this clone has also been sequenced (SEQ ID No:3). The predicted amino acid sequence (SEQ ID No:4) revealed the same motifs identified in SEQ ID No: 2.

The protein kinase domain carries 11 subdomains containing 15 conserved residues diagnostic of protein kinases and is flanked by a 31 aa juxtamembrane domain (aa 677–707) and a C terminus domain. The presumed intron is located between the two highly conserved residues P and E (aa 879 and aa 880) in the putative catalytic domain. The consensus sequences present in subdomains VI (DIKSSN; SEQ ID No:13) and VIII (GTIGYAAPE; SEQ ID No:14) strongly suggest that Xa-21 has serine/threonine kinase (as opposed to tyrosine) activity.

Previous work has demonstrated that phosphorylated RLK5 protein interacts with the kinase interacting domain (KID) of a type 2C serine-threonine protein phosphatase (Stone et al., *Science* 266:793–795 (1994)). The KID binds the phosphorylated LRR containing proteins, RLK5 and TMK1, but fails to bind the S-related receptor kinases ZmpK1 and RLK4. These results suggests that the Arabidopsis KID is functionally analogous to the SH2 domain of animal proteins. Sequence alignment of the Arabidopsis receptor like kinases RLK5, TMK1 with Xa-21 reveals a set of conserved amino acids (N/Q)X(L/V)S(G/S)(L/A)(FIV) (P/E) (SEQ ID No:15) surrounding a serine residue that is carboxy terminal to the last residue (argine) higly conserved in all protein kinases (position 999 in Xa21 gene prodcut). The carboxyl terminal position of this consensus in these proteins is similar to the carboxyl terminal phosphotyrosine of the Rous sarcoma virus oncogene product pp60 c-Src which is essential for binding to SH2 domain containing proteins. These conserved amino acids are lacking in the S related receptor kinases ZmpK1, RLK4 and SRK6 and in intracellular kinases which do not bind KID. Thus, this region act as a high affinity and specific binding site for proteins containing KID. Modification of the amino acid sequence of this region of Xa21 can thus be used to alter affinity for the KID protein and thus control intracellular signalling in response to ligand binding of the LRR domain.

EXAMPLE 3

Plant Transformation Using Xa21 Genes

The Xa21 genes described above were used to transform rice plants to demonstrate that the genes could confer Xanthomonas resistance to susceptible plants. The genes were introduced into susceptible rice strains using a variation of the methods of Li et al, *Plant Cell Rep.* 12:250–255 (1993). Briefly, co-transformation was carried out using the hygromycin construct pMON410 (from Monsanto) and a bluescript vector containing the sequences of interest. In addition, the Kpn fragment of pB822 was cloned into the pTA818 vector, which is derived from Invitrogen vector per 1000 and contains the 1 kb fragment RAPD818 (Ronald et al., supra). The resulting plasmid is referred to as pC822. The plants were selected on hygromycin (30 mg/L) and then screened for resistance to Xoo race 6.

Standard methods were used to test Xanthomonas resistance in the transformants. The assays were carried out according to the methods of Kaufman et al *Plant Disease Rep.* 57:537–541 (1973). Briefly, Xoo race 6 was grown on PSA plates for 3 days. The bacteria were scraped up, resuspended in water and the OD adjusted to $10^9$ colony forming units per ml. Scissors were dipped in the suspension and leaves from the transformed plants (4 months post bombardment) were cut 5 cm from the tip. Plants were scored for the presence of lesions 11 days post inoculation.

FIG. 4 shows lesion length data from experiments using an expression vector comprising the gene from the pC822 clone. Individuals derived from independent transformants 106-1, -4, -17 and -22 carry the pC822 construct and showed increased resistance as compared to susceptible untransformed controls (IR24), as well as rice plants transformed with putative blast-resistance gene Pi7. Individuals derived from independent transformant 106-26 carry parts of the pC822 construct but did not show increased resistance as compared to the controls.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An isolated nucleic acid construct comprising a Xa21 polynucleotide sequence of greater than about fifty nucleotides, which polynucleotide sequence hybridizes to SEQ ID NO:1 or to SEQ ID NO:3 under stringent conditions.

2. The nucleic acid construct of claim 1, wherein the Xa21 polynucleotide sequence encodes an Xa21 polypeptide having an leucine rich repeat motif.

3. The nucleic acid construct of claim 1, wherein the Xa21 polynucleotide sequence encodes an Xa21 polypeptide having a cytoplasmic protein kinase domain.

4. The nucleic acid construct of claim 1, wherein the Xa21 polynucleotide sequence encodes an Xa21 polypeptide as shown in SEQ ID No:2.

5. The nucleic acid construct of claim 1, wherein the Xa21 polynucleotide sequence encodes an Xa21 polypeptide as shown in SEQ ID No:4.

6. The nucleic acid construct of claim 1, wherein the polynucleotide sequence is a full length Xa21 gene.

7. The nucleic acid construct of claim 1, wherein the Xa21 polynucleotide is as shown in SEQ ID No:1.

8. The nucleic acid construct of claim 1, wherein the Xa21 polynucleotide is as shown in SEQ ID No:3.

9. The nucleic acid construct of claim 1, further comprising a promoter operably linked to the Xa21 polynucleotide sequence.

10. The nucleic acid construct of claim 9, wherein the promoter is a tissue-specific promoter.

11. The nucleic acid construct of claim 9, wherein the promoter is a constitutive promoter.

12. A nucleic acid construct comprising a promoter sequence greater than about fifty nucleotides which hybridizes under stringent conditions to SEQ ID NO:1 or SEO ID NO:3, which promoter is linked to a heterologous polynucleotide sequence.

13. A transgenic plant comprising the nucleic acid construct of claim 12.

14. The transgenic plant of claim 13, wherein the plant is rice.

15. The transgenic plant of claim 13, wherein the plant is tomato.

16. The transgenic plant of claim 13, wherein the polynucleotide sequence encodes an Xa21 polypeptide as shown in SEQ ID NO:2 or SEQ ID NO:4.

17. A method of enhancing resistance to Xanthomonas in a plant, the method comprising introducing into the plant a recombinant expression cassette comprising a plant promoter operably linked to the nucleic acid construct of claim 1.

18. The method of claim 17, wherein the plant tissue is from rice.

19. The method of claim 17, wherein the plant tissue is from tomato.

20. The method of claim 17, wherein the polynucleotide sequence encodes an Xa21 polypeptide as shown in SEQ ID NO:2 or SEQ ID NO:4.

21. The method of claim 17, wherein the promoter is a tissue-specific promoter.

22. The method of claim 17, wherein the promoter is a constitutive promoter.

23. The method of claim 17, wherein the method comprises introducing into the plant a recombinant expression cassette comprising a plant promoter operably linked to a polynucleotide sequence as shown in SEQ ID NO:3.

24. The method of claim 20, wherein the polynucleotide sequence encodes an Xa21 polypeptide as shown in SEQ ID NO:4.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 6256 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: join(1648..4383, 5178..5513)
( D ) OTHER INFORMATION: /product="RRK-F"
/ note= "Xa21 Xanthomonas spp. disease -continued resistance gene RRK-F from rice (Oryza sativa)"

( x i ) SEQUENCE DESCRIPTION: SEQ ID NO:1:

| | | | | | |
|---|---|---|---|---|---|
| AAGCTTTCTA | AATTATTTAA | CTCTAAGTCT | GTTATTATCC | CCAAGTACAT | CATCATCATA | 60 |
| CATAATATTT | CATATTCACG | ACATCCTTAA | GCTAGATGCT | TTTGGCCATT | CTCTTATCTT | 120 |
| TTTAAAGAAA | TTCTCTCCCA | ATTAAGATGA | GAGTGTCTTC | TAGCAATTTG | CCAGTTTTTA | 180 |
| CAATGTCTTT | GAGTCCTCAC | ACATTTTCAT | GATGTTACCA | ATAAATTACG | GACGCCGTGT | 240 |
| TTAGTTCTAA | AGTTTTTCTT | CAAACTTACA | ACTTTTCAAT | CGCATCAAAA | CTTTCTCCTA | 300 |
| CACACACAAA | CTTTCAACTT | TTCCATCACA | TCGTTCCAAT | TTCAACCAAA | CTTCCAATTT | 360 |
| TGGTATGAAC | TAAACACAGC | CGAAAACAAA | ATCTGTGTGT | TATGGCCCTG | TTTAGATTCT | 420 |
| AACTTTTCCA | TTACATCAAA | CTTTCCTACA | TACACGAACT | TTCAACTTTT | CCGTCACATC | 480 |
| GTTTCAATTT | TTTAAAACTT | CCATTTTTAA | CGTGGAACTA | AACACAACCT | ATATAACGGA | 540 |
| ATTTGTCAAA | AACTCAATGG | TGAAAGTCAC | ACCTCACAGG | AAGGGCGCGC | TCTAGTCAAG | 600 |
| ACATCATTAA | ACAGGTACAC | AGGTTGTACT | AGCTTGTCAT | GTTTATCTTG | CGTCTGCGAG | 660 |
| ACGTAAATCC | ATGCCAAACA | AAAGTGCTTC | TATAGAGATA | TCATAAGGAT | ATGGTTTGGG | 720 |
| GCCATATCCA | ACTGCTCAGG | AGAGATCTCG | TTCGGAGGTG | AGGTTAGATG | TTCACCTCTC | 780 |
| CACACATAAC | GAAGGCGATC | TTCTTCGCAT | ATGATTAGGC | ATTAGATAAA | ATAACCTTAA | 840 |
| AAAATAAATC | AATATGATTT | TTTTAGAAAA | AAATTATATA | CACTAAGTAT | AAGCATTGTC | 900 |
| AAGGAGGAAG | AAACACACAC | TCCCATATAG | AGAGATAGAA | ACATAGCTAT | AGGTAGTGTC | 960 |
| ACTGAGTATT | TTCCATCACG | CATATCCATA | TAAAATTAGG | GGGTGTTACA | TCCATAGGTG | 1020 |
| TAAAGTTTTG | GCATGTTATA | TCGAGTATTA | CGTAGAATGC | CGTATTAGGT | GTCCGGGCAC | 1080 |
| TAATAAAAAA | ATAATTACAG | AATCCGTTAG | TAAACCGCGA | GATAAATTTA | TTAAGCCTAA | 1140 |
| TTAATCCCAT | CATTAACAAA | TGTTTACCGT | AGCACCACAT | TGTCAAATCA | TGGAGCAATT | 1200 |
| AGGTTTAAAA | GATTCGTCTC | GCAAATTAGT | CATAATCTGT | GCAATTAGTT | ATTTTAGAC | 1260 |
| TATATTTAAG | ACTTCGTACA | GGTGTTCAAA | CGTTCGATGT | GACATGGTGC | AAAATTTTAG | 1320 |
| GGTGTCATCT | AGACACTCCC | TTAATTAGAA | AGTTAGGAAG | AGGCGGTAAA | GAACGCAGCA | 1380 |
| TGACTGAAAC | TTTGAAAATT | TGATAAGGTA | CACCAACTGG | AGTATCTTTT | ATTTTCATTG | 1440 |
| AAGACTTTGA | CCAGAAGAGC | TTGACCCGTT | TTTCTTGGAG | TAGCCAGTAA | TGTTTCATTC | 1500 |
| TTTTCCTTTT | GCTGGGACTT | CTTTTTATTT | TTTTGACAG | GAGCCATTTG | TTGGGACTTG | 1560 |
| GGATCCCTTT | ACTGTTATAG | GACCAGTGCT | TGAATCCAAA | CACTGCATTG | ATCAGCTCAG | 1620 |
| CTCATTGTAG | CGCACTCCTC | CGCATGCATG | GCGAGATCAC | CAACGTCGGT | CATGATCTCT | 1680 |
| TCTTTGCTGC | TGCTGCTGTT | GATCGGCCCA | GCGAGCAGTG | ACGATGATGC | TGCTGCTGCT | 1740 |
| GCTGCTCGTA | CCAGTACAGG | CGGCGTCGCG | GCGACGAACT | CGCGCTGCTC | TCTTTCAAGT | 1800 |
| CATCCCTGCT | ACACCAGGGG | GGCTTGTACG | CTGGCATCTT | GGAACACGTC | CGGCCACGGC | 1860 |
| CAGCACTGCA | CATGGGTGGG | TGTTGTGTGC | GGCCGCGCGC | GCCGGCACCC | ACACAGGGTG | 1920 |
| GTGAAGCTGC | TGCTGCGCTC | GTCCAACCTG | TCCGGGATCA | TCTCGCCGTC | GCTGGGCAAC | 1980 |
| CTGTCCTTCC | TCAGGGAGCT | GGACCTCAGC | GACAACTACC | TCTCCGGCGA | GATACCACCG | 2040 |
| GAGCTCAGCC | GTCTCAGCAG | GCTTCAGCTG | CTGGAGCTGA | GCGGTAACTC | CATCCAAGGG | 2100 |
| AGCATCACG | CGGCCATTGG | AGCATGCACC | AAGTTGACAT | CGCTAGACCT | CAGCCACAAC | 2160 |
| CAACTGAGAT | TGGTGCCAGC | TGAAACATCT | CTCGAATTTG | TACCTTCACA | CCAATGGTTA | 2220 |
| TGTCAGGAGA | GATTCCATCT | GATTTTGGGC | AATCTCACTA | CGCCTTCAGT | ATTTGATTTG | 2280 |

```
ACCTGCAACA GATTATCACG GAGCTATACC TTCATCGCTA GGGCAGCTCA GCAGCAGTCT   2340
ATTGACTATG AATTTGTGC  TACGAACAAT CTAACTGGCA TGATCCCCAA TTCTATCTGG   2400
AACCTTTCGT CTCTAGCAGC GTTTAGCTGT CAAGCGAAAA ACAAGCTAGG TGGTATGATC   2460
CCTACAAATG CATTCAAAAC CCTTCACCTC CTCGAGGTGG TAGATATGGG CACTAACCGA   2520
TTCCATGGCA AAATCCCTGC CTCAGTTGCT AATGCTTCTC ATCTGACACG GCTTCAGATT   2580
GATGGCAACT TGTTCAGTGG AATTATCACC TCGGGGTTTG GAAGGTTAAG AAATCTCACA   2640
ACACTGTATC TCTGGAGAAA TTTGTTTCAA ACTAGAGAAC AAGAAGATTG GGGGTTCATT   2700
TCTGACCTAA CAAATTGCTC CAAATTACAA ACATTGGACT TGGGAGAAAA TAACCTGGGG   2760
GGAGTTCTTC CTAATTCGTT TTCCAATCTT TCCACTTCGC TTAGTTTTCT TGCACTTGAT   2820
TTGAATAAGA TCACAGGAAG CATTCCAAAG GATATTGGCA ATCTTATTGG CTTACAACAT   2880
CTCTATCTCT GCAACAACAA TTTCAGAGGG TCACTTCCAT CATCGTTGGG CAGGCTTAGA   2940
AACTTAGGCA TTCTAGTCGC CTACGAAAAC AACTTGAGCG GTTCGATCCC ATTGGCCATA   3000
GGAAATCTTA CTGAACTTAA TATCTTACTG CTCGGCACCA ACAAATTCAG TGGTTGGATA   3060
CCATACACAC TCTCAAACCT CACAAACTTG TTGTCATTAG GCCTCTCGCA CCTCGCACCA   3120
CAATCAGGGT TGGATACCTA CACATCTCAA CCTCACAACT GTGTCATAGC CTTCACTATA   3180
CCTAGTGGGT CCCAAATACC CCAGGTGAAA TTAATTCAAA TAGTCCAAAC ACCTATCAAA   3240
AAGATGATCA ATGTATCAAA AAATACACTT GGAGGGATCA GATACCCACA AGAAATAGGG   3300
CATCTCAAAA ATCTAGTAGA ATTCATGCAG AATCGAATAG ATATCAGTAA AATCCCTAAC   3360
ACGCTTGGTG ATTGCCAGCT CTTACGGTAT CTTTATCTGC AAAATAATTT GTTATCTGGT   3420
AGCATCCCAT CAGCCTTGGG TCAGCTGAAA GGTCTCGAAA CTCTTGATCT CTCAAGCAAC   3480
AATTTGTCAG GCCAGATACC CACATCCCTT AGCAGATATT ACTATGCTTC ATTCCTTGAA   3540
CCTTTCTTTC AACAGCTTTG TGGGGAAGT  GCCAACCATT GCGTGCTTTC GCAGATGCAT   3600
CCGGGATCTC AATCCAAGGC AATGCCAAAC TCTGTGGTGG AATACCTGAT CTACATCTGC   3660
CTCGATGTTG TCCCATTACT AGAGAACAGA AAGCATTTTC CAGCTCTACC TATTTCTGTT   3720
TCTCTGGTCG CAGCACTGGC CATCCTCTCA TCACTCTACT TGCTTATAAC CTGGAACAAG   3780
AGAACTAAAA AGGGAGCCCC TTCAAGAACT TCCATGAAAG GCCACCATT  GGTCTCTTAT   3840
CCGCAGTTGG TAAAAGCAAC AGATGGTTTC GCGCCGACCA ATTTGTTGGG TTCTGGATCA   3900
TTTGCCTCAG TATACAAACG AAAGCTTGAA AATCCTAAGG CACTCAAGAG TTTCACTGCC   3960
GAATGTGAAG CACTACGAAA TATGCGACAT CGAAATCTTG TCAAGATAGT TACAATTTGC   4020
TCGAGCATTG ATAACAGAGG GAACGATTTC AAAGCAATTG TGTATGACTT CATGCCCAAC   4080
GGCAGTCTGG AAGATTGGAT ACACCCTGAA ACAAATGATC AAGCAGACCA GAGGCACTTG   4140
AATCTGCATC GAAGAGTGAC CATACTACTT GATGTTGCCT GTGCATTGGA CTATCTTCAC   4200
CGCCATGGCC CTGAACCTGT TGTACACTGT GATGTTAAAT CAAGCAATGT GCTGTTAGAT   4260
TCTGATATGG TAGCGCATGT TGGAGATTCT GGGCTTGCAA GAATACTTGT TGATGGGACC   4320
TCATTGATAC AACAGTCAAC AAGCTCGATG GGATTTAGAG GACAATTGG  CTATGCAGCA   4380
CCAGGTCAGC AAGTCCTTCC AGTATTTGC  ATTTTCTGAT CTCTAGTGCT ATATGAAATA   4440
GTTTTTACCT CTAGTGAAAC TGATGGAGAA TATAAGTAAT TAATTGAACT AATTAAATTG   4500
CACAAAAATA AGATTATTTG CCATATCTAT TCAGATGCTA AATATAGCTA GTTCATAGAG   4560
GTACATATTT TTTTTATATA GGAATCTAGA GCTACTACAC ACTCAAATCA AATTATGGGT   4620
GTTTTCTGCT CTACACTGCA ATATGAAATG ATTATCAGAA GGATCAAATT TGAGTAAATT   4680
```

-continued

| | | | | | |
|---|---|---|---|---|---|
| TGTCAATTCT | ACATTTAAGA | AACACTTTTT | TTTGTATGTA | CTAGTTATTA | CAATTTTTTA | 4740
| TTTCAAGAAC | TTGCATTGAC | CATGAAAAGT | ACTTGGTACT | ACTTCTAATT | CCCACATGGA | 4800
| GGTGGTGAAA | ATAATATAGA | TACAAAAACG | AAGTATCATA | TGTTGTGTGA | TATACTATAA | 4860
| TCACAATGAA | CACAAACAGG | ATTCGTACAA | AAGTAATTGG | CCATCATAGC | AACTGATTGC | 4920
| TTGGGGTAAC | TGTATAGCAC | AATCATACCA | AATTTCTTTA | GATATGTATT | TGTAAATTAG | 4980
| ATTCTTAAAG | TTAAATATGA | AATTTCATTG | GTATTTATGT | TTCTTTATAT | AATAAAAATT | 5040
| AATCCAACCT | TTACATCTAC | CATTTGTCCA | GCCATCCTTG | TTATTTGTGA | TATTTAACAC | 5100
| GTAATTTTAC | ATAATTATAC | ATCCAAGTTC | TTTTTATTTA | ACACTGGAAA | TTTGAAATCG | 5160
| TATTTCCTAC | TCAAACAGAG | TATGGCGTCG | GGCACATTGC | ATCAACACAT | GGAGATATTT | 5220
| ACAGCTATGG | AATTCTAGTG | CTGGAAATAG | TAACCGGGAA | GCGGCCAACT | GACAGTACAT | 5280
| TCAGACCCGA | TTTGGGCCTC | CGTCAGTACG | TTGAACTGGG | CCTACATGGC | AGAGTGACGG | 5340
| ATGTTGTTGA | CACGAAGCTC | ATTTTGGATT | CTGAGAACTG | GCTGAACAGT | ACAAATAATT | 5400
| CTCCATGTAG | AAGAATCACT | GAATGCATTG | TTTCGCTGCT | TAGACTTGGG | TTGTCTTGCT | 5460
| CTCAGGATTT | SCCATTGAGT | AGACGCCACC | CGGAGATATC | ACCGACGAAC | TGAATGCCAT | 5520
| CAAACAGAAT | CTCTCCGGAG | TTGTTTCCAG | TGTGTGAAGG | TGCGAGCCTC | GAATTCTGAT | 5580
| GTTATGTCTT | GTAATGTTTT | ATTGCCACTA | GTCTTCAGAT | TGGAATGCTC | TTCCGATCAG | 5640
| ACTTCTTCAG | TGGTATCTAC | CACACGATCA | CTAAAGTCAT | CGTGGCTATT | TCCTGATCCA | 5700
| GCATATCTGA | TCATGCATGT | TCTGTGTTTT | ATACCTGTAT | TTTACTCTGA | ATTGCCACAC | 5760
| CTCAACCCTG | CCTCTGTTTG | TTTGGCATAC | AAAAGATAGT | GATGAGTATA | TTGTTTCAGG | 5820
| GGCTTCCTAG | TTGGCGTGTG | TGCTTACCGG | CACGCACGCA | GCCCGAGGGT | GGGTTTCTTT | 5880
| TTTTTTCCAT | TGTTATTCCG | TTGCTTTTTT | CCACCACGGT | AGATTTTTT | TTTCTGGATT | 5940
| TCCATTTTTT | CCGTTGTTTT | TCTCTATCGC | TTATGCTGGC | GGATTTTTTT | CCGTGGTTTT | 6000
| TTTTTCAAGA | CGAGTATATC | TAATGTAACT | AACATGTTAC | TTTTAGATAA | CGATGGTTAT | 6060
| TAAGATAAGA | TTTTTTTCTG | GAAGATTTTT | GTAAGTAAAT | GGTAAAAAAT | ATGGAAATGG | 6120
| AAACGGAAAT | AGTTTTGCTG | TTATACCGAT | CGTTTCCATA | TTTACCGTAT | TCTTATAGAA | 6180
| ATTACCGTNT | CTTATAATAT | GGTAATTACC | GTATTTCTAA | ATATGTTGAT | ATCGATTTTG | 6240
| CTATATATTT | GTCGAC | | | | | 6256

( 2 ) INFORMATION FOR SEQ ID NO:2:

( i ) SEQUENCE CHARACTERISTICS:
        ( A ) LENGTH: 1023 amino acids
        ( B ) TYPE: amino acid
        ( C ) STRANDEDNESS:
        ( D ) TOPOLOGY: linear ( i i ) MOLECULE TYPE: protein ( i x ) FEATURE:
        ( A ) NAME/KEY: Protein
        ( B ) LOCATION: 1..1023
        ( D ) OTHER INFORMATION: /note= "Xa21 Xanthomonas spp.
            disease resistance polypeptide RRK-F
            from rice (Oryza sativa)"

( i x ) FEATURE:
        ( A ) NAME/KEY: Modified-site
        ( B ) LOCATION: 1010
        ( D ) OTHER INFORMATION: /note= "Xaa = Leu when position
            5471 of RRK- F = G or Phe when position
            5471 of RRK- F = C"

( x i ) SEQUENCE DESCRIPTION: SEQ ID NO:2:

| Met | Ala | Arg | Ser | Pro | Thr | Ser | Val | Met | Ile | Ser | Ser | Leu | Leu | Leu | Leu |
|---|---|---|---|---|---|---|---|---|---|---|---|---|---|---|---|
| 1 | | | | 5 | | | | | 10 | | | | | 15 | |

| Leu | Leu | Ile | Gly | Pro | Ala | Ser | Ser | Asp | Asp | Ala | Ala | Ala | Ala | Ala |
|---|---|---|---|---|---|---|---|---|---|---|---|---|---|---|
| | | | 20 | | | | | 25 | | | | | 30 | |

| Ala | Arg | Thr | Ser | Thr | Gly | Gly | Val | Ala | Ala | Thr | Asn | Ser | Arg | Cys | Ser |
|---|---|---|---|---|---|---|---|---|---|---|---|---|---|---|---|
| | | 35 | | | | | 40 | | | | | 45 | | | |

| Leu | Ser | Ser | His | Pro | Cys | Tyr | Thr | Arg | Gly | Ala | Cys | Thr | Leu | Ala | Ser |
|---|---|---|---|---|---|---|---|---|---|---|---|---|---|---|---|
| | 50 | | | | | 55 | | | | | 60 | | | | |

| Trp | Asn | Thr | Ser | Gly | His | Gly | Gln | His | Cys | Thr | Trp | Val | Gly | Val | Val |
|---|---|---|---|---|---|---|---|---|---|---|---|---|---|---|---|
| 65 | | | | | 70 | | | | 75 | | | | | | 80 |

| Cys | Gly | Arg | Ala | Arg | Arg | His | Pro | His | Arg | Val | Val | Lys | Leu | Leu | Leu |
|---|---|---|---|---|---|---|---|---|---|---|---|---|---|---|---|
| | | | | 85 | | | | | 90 | | | | | 95 | |

| Arg | Ser | Ser | Asn | Leu | Ser | Gly | Ile | Ile | Ser | Pro | Ser | Leu | Gly | Asn | Leu |
|---|---|---|---|---|---|---|---|---|---|---|---|---|---|---|---|
| | | | 100 | | | | | 105 | | | | | 110 | | |

| Ser | Phe | Leu | Arg | Glu | Leu | Asp | Leu | Ser | Asp | Asn | Tyr | Leu | Ser | Gly | Glu |
|---|---|---|---|---|---|---|---|---|---|---|---|---|---|---|---|
| | | | 115 | | | | | 120 | | | | | 125 | | |

| Ile | Pro | Pro | Glu | Leu | Ser | Arg | Leu | Ser | Arg | Leu | Gln | Leu | Leu | Glu | Leu |
|---|---|---|---|---|---|---|---|---|---|---|---|---|---|---|---|
| | | 130 | | | | | 135 | | | | | 140 | | | |

| Ser | Gly | Asn | Ser | Ile | Gln | Gly | Ser | Ile | His | Ala | Ala | Ile | Gly | Ala | Cys |
|---|---|---|---|---|---|---|---|---|---|---|---|---|---|---|---|
| 145 | | | | | 150 | | | | | 155 | | | | | 160 |

| Thr | Lys | Leu | Thr | Ser | Leu | Asp | Leu | Ser | His | Asn | Gln | Leu | Arg | Leu | Val |
|---|---|---|---|---|---|---|---|---|---|---|---|---|---|---|---|
| | | | | 165 | | | | | 170 | | | | | 175 | |

| Pro | Ala | Glu | Thr | Ser | Leu | Glu | Phe | Val | Pro | Ser | His | Gln | Trp | Leu | Cys |
|---|---|---|---|---|---|---|---|---|---|---|---|---|---|---|---|
| | | | 180 | | | | | 185 | | | | | 190 | | |

| Gln | Glu | Arg | Phe | His | Leu | Ile | Leu | Gly | Asn | Leu | Thr | Thr | Pro | Ser | Val |
|---|---|---|---|---|---|---|---|---|---|---|---|---|---|---|---|
| | | 195 | | | | | 200 | | | | | 205 | | | |

| Phe | Asp | Leu | Thr | Cys | Asn | Arg | Leu | Ser | Arg | Ser | Tyr | Thr | Phe | Ile | Ala |
|---|---|---|---|---|---|---|---|---|---|---|---|---|---|---|---|
| | 210 | | | | | 215 | | | | | 220 | | | | |

| Arg | Ala | Ala | Gln | Gln | Gln | Ser | Ile | Asp | Tyr | Glu | Phe | Cys | Ala | Thr | Asn |
|---|---|---|---|---|---|---|---|---|---|---|---|---|---|---|---|
| 225 | | | | | 230 | | | | | 235 | | | | | 240 |

| Asn | Leu | Thr | Gly | Met | Ile | Pro | Asn | Ser | Ile | Trp | Asn | Leu | Ser | Ser | Leu |
|---|---|---|---|---|---|---|---|---|---|---|---|---|---|---|---|
| | | | | 245 | | | | | 250 | | | | | 255 | |

| Ala | Ala | Phe | Ser | Cys | Gln | Ala | Lys | Asn | Lys | Leu | Gly | Gly | Met | Ile | Pro |
|---|---|---|---|---|---|---|---|---|---|---|---|---|---|---|---|
| | | | 260 | | | | | 265 | | | | | 270 | | |

| Thr | Asn | Ala | Phe | Lys | Thr | Leu | His | Leu | Leu | Glu | Val | Val | Asp | Met | Gly |
|---|---|---|---|---|---|---|---|---|---|---|---|---|---|---|---|
| | | 275 | | | | | 280 | | | | | 285 | | | |

| Thr | Asn | Arg | Phe | His | Gly | Lys | Ile | Pro | Ala | Ser | Val | Ala | Asn | Ala | Ser |
|---|---|---|---|---|---|---|---|---|---|---|---|---|---|---|---|
| | | 290 | | | | | 295 | | | | | 300 | | | |

| His | Leu | Thr | Arg | Leu | Gln | Ile | Asp | Gly | Asn | Leu | Phe | Ser | Gly | Ile | Ile |
|---|---|---|---|---|---|---|---|---|---|---|---|---|---|---|---|
| 305 | | | | | 310 | | | | | 315 | | | | | 320 |

| Thr | Ser | Gly | Phe | Gly | Arg | Leu | Arg | Asn | Leu | Thr | Thr | Leu | Tyr | Leu | Trp |
|---|---|---|---|---|---|---|---|---|---|---|---|---|---|---|---|
| | | | | 325 | | | | | 330 | | | | | 335 | |

| Arg | Asn | Leu | Phe | Gln | Thr | Arg | Glu | Gln | Glu | Asp | Trp | Gly | Phe | Ile | Ser |
|---|---|---|---|---|---|---|---|---|---|---|---|---|---|---|---|
| | | | 340 | | | | | 345 | | | | | 350 | | |

| Asp | Leu | Thr | Asn | Cys | Ser | Lys | Leu | Gln | Thr | Leu | Asp | Leu | Gly | Glu | Asn |
|---|---|---|---|---|---|---|---|---|---|---|---|---|---|---|---|
| | | 355 | | | | | 360 | | | | | 365 | | | |

| Asn | Leu | Gly | Gly | Val | Leu | Pro | Asn | Ser | Phe | Ser | Asn | Leu | Ser | Thr | Ser |
|---|---|---|---|---|---|---|---|---|---|---|---|---|---|---|---|
| | | 370 | | | | | 375 | | | | | 380 | | | |

| Leu | Ser | Phe | Leu | Ala | Leu | Asp | Leu | Asn | Lys | Ile | Thr | Gly | Ser | Ile | Pro |
|---|---|---|---|---|---|---|---|---|---|---|---|---|---|---|---|
| 385 | | | | | 390 | | | | | 395 | | | | | 400 |

| Lys | Asp | Ile | Gly | Asn | Leu | Ile | Gly | Leu | Gln | His | Leu | Tyr | Leu | Cys | Asn |
|---|---|---|---|---|---|---|---|---|---|---|---|---|---|---|---|
| | | | | 405 | | | | | 410 | | | | | 415 | |

```
Asn  Asn  Phe  Arg  Gly  Ser  Leu  Pro  Ser  Ser  Leu  Gly  Arg  Leu  Arg  Asn
               420                 425                      430

Leu  Gly  Ile  Leu  Val  Ala  Tyr  Glu  Asn  Asn  Leu  Ser  Gly  Ser  Ile  Pro
          435                 440                      445

Leu  Ala  Ile  Gly  Asn  Leu  Thr  Glu  Leu  Asn  Ile  Leu  Leu  Gly  Thr
     450                 455                      460

Asn  Lys  Phe  Ser  Gly  Trp  Ile  Pro  Tyr  Thr  Leu  Ser  Asn  Leu  Thr  Asn
465                      470                      475                           480

Leu  Leu  Ser  Leu  Gly  Leu  Ser  His  Leu  Ala  Pro  Gln  Ser  Gly  Leu  Asp
               485                 490                                495

Thr  Tyr  Thr  Ser  Gln  Pro  His  Asn  Cys  Val  Ile  Ala  Phe  Thr  Ile  Pro
               500                 505                      510

Ser  Gly  Ser  Gln  Ile  Pro  Gln  Val  Lys  Leu  Ile  Gln  Ile  Val  Gln  Thr
          515                 520                      525

Pro  Ile  Lys  Lys  Met  Ile  Asn  Val  Ser  Lys  Asn  Thr  Leu  Gly  Gly  Ile
     530                 535                      540

Arg  Tyr  Pro  Gln  Glu  Ile  Gly  His  Leu  Lys  Asn  Leu  Val  Glu  Phe  Met
545                      550                      555                           560

Gln  Asn  Arg  Ile  Asp  Ile  Ser  Lys  Ile  Pro  Asn  Thr  Leu  Gly  Asp  Cys
               565                 570                           575

Gln  Leu  Leu  Arg  Tyr  Leu  Tyr  Leu  Gln  Asn  Asn  Leu  Leu  Ser  Gly  Ser
          580                 585                      590

Ile  Pro  Ser  Ala  Leu  Gly  Gln  Leu  Lys  Gly  Leu  Glu  Thr  Leu  Asp  Leu
               595                 600                      605

Ser  Ser  Asn  Asn  Leu  Ser  Gly  Gln  Ile  Pro  Thr  Ser  Leu  Ser  Arg  Tyr
     610                 615                      620

Tyr  Tyr  Ala  Ser  Phe  Leu  Glu  Pro  Phe  Phe  Gln  Gln  Leu  Cys  Gly  Gly
625                      630                      635                           640

Ser  Ala  Asn  His  Cys  Val  Leu  Ser  Gln  Met  His  Pro  Gly  Ser  Gln  Ser
               645                 650                           655

Lys  Ala  Met  Pro  Asn  Ser  Val  Val  Glu  Tyr  Leu  Ile  Tyr  Ile  Cys  Leu
               660                 665                      670

Asp  Val  Val  Pro  Leu  Leu  Glu  Asn  Arg  Lys  His  Phe  Pro  Ala  Leu  Pro
          675                 680                      685

Ile  Ser  Val  Ser  Leu  Val  Ala  Ala  Leu  Ala  Ile  Leu  Ser  Ser  Leu  Tyr
     690                 695                      700

Leu  Leu  Ile  Thr  Trp  Asn  Lys  Arg  Thr  Lys  Lys  Gly  Ala  Pro  Ser  Arg
705                      710                      715                           720

Thr  Ser  Met  Lys  Gly  His  Pro  Leu  Val  Ser  Tyr  Pro  Gln  Leu  Val  Lys
                    725                 730                           735

Ala  Thr  Asp  Gly  Phe  Ala  Pro  Thr  Asn  Leu  Leu  Gly  Ser  Gly  Ser  Phe
               740                 745                           750

Ala  Ser  Val  Tyr  Lys  Arg  Lys  Leu  Glu  Asn  Pro  Lys  Ala  Leu  Lys  Ser
          755                 760                      765

Phe  Thr  Ala  Glu  Cys  Glu  Ala  Leu  Arg  Asn  Met  Arg  His  Arg  Asn  Leu
     770                 775                      780

Val  Lys  Ile  Val  Thr  Ile  Cys  Ser  Ser  Ile  Asp  Asn  Arg  Gly  Asn  Asp
785                      790                      795                           800

Phe  Lys  Ala  Ile  Val  Tyr  Asp  Phe  Met  Pro  Asn  Gly  Ser  Leu  Glu  Asp
                    805                 810                           815

Trp  Ile  His  Pro  Glu  Thr  Asn  Asp  Gln  Ala  Asp  Gln  Arg  His  Leu  Asn
               820                 825                      830

Leu  His  Arg  Arg  Val  Thr  Ile  Leu  Leu  Asp  Val  Ala  Cys  Ala  Leu  Asp
               835                 840                      845
```

Tyr  Leu  His  Arg  His  Gly  Pro  Glu  Pro  Val  Val  His  Cys  Asp  Val  Lys
     850            855                      860

Ser  Ser  Asn  Val  Leu  Leu  Asp  Ser  Asp  Met  Val  Ala  His  Val  Gly  Asp
865                 870                      875                           880

Ser  Gly  Leu  Ala  Arg  Ile  Leu  Val  Asp  Gly  Thr  Ser  Leu  Ile  Gln  Gln
               885                      890                           895

Ser  Thr  Ser  Ser  Met  Gly  Phe  Arg  Gly  Thr  Ile  Gly  Tyr  Ala  Ala  Pro
               900                      905                           910

Glu  Tyr  Gly  Val  Gly  His  Ile  Ala  Ser  Thr  His  Gly  Asp  Ile  Tyr  Ser
          915                      920                      925

Tyr  Gly  Ile  Leu  Val  Leu  Glu  Ile  Val  Thr  Gly  Lys  Arg  Pro  Thr  Asp
          930                      935                      940

Ser  Thr  Phe  Arg  Pro  Asp  Leu  Gly  Leu  Arg  Gln  Tyr  Val  Glu  Leu  Gly
945                      950                      955                      960

Leu  His  Gly  Arg  Val  Thr  Asp  Val  Val  Asp  Thr  Lys  Leu  Ile  Leu  Asp
               965                      970                           975

Ser  Glu  Asn  Trp  Leu  Asn  Ser  Thr  Asn  Asn  Ser  Pro  Cys  Arg  Arg  Ile
               980                      985                      990

Thr  Glu  Cys  Ile  Val  Ser  Leu  Leu  Arg  Leu  Gly  Leu  Ser  Cys  Ser  Gln
          995                      1000                     1005

Asp  Xaa  Pro  Leu  Ser  Arg  Arg  His  Pro  Glu  Ile  Ser  Pro  Thr  Asn
     1010                     1015                     1020

( 2 ) INFORMATION FOR SEQ ID NO:3:

( i ) SEQUENCE CHARACTERISTICS:
        ( A ) LENGTH: 5992 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(512..3149, 3993..4393)
        ( D ) OTHER INFORMATION: /product="RRK-B"
                / note= "Xa21 Xanthomonas spp. disease
                resistance gene RRK-B from rice (Oryza
                sativa)"

( x i ) SEQUENCE DESCRIPTION: SEQ ID NO:3:

```
TCTTCTCAAA  CACGGCATTG  GATGCTCTCA  TAGCACTTGC  TCGTTCGGAT  AGAAGACTTG      60

ACGAAGACGA  CCGCTACAAC  TTGGTGTGTT  ATATCGTGCT  TTGTTTAGCA  TAATCATTAC     120

ATATATTCCA  TGCCGAAGTG  CCGACGATGA  GACCGTGTTC  GATGCATCTT  TGTATGGCAT     180

CTAGGGACAA  AGAGCATAGA  GTCCCTACCA  TAGTACCAGC  TCGCGCAGAA  GACTTGACGA     240

GAAGACCGAC  TGCTACACCT  TGGTGTGTAA  TAATATCGTG  TTGTGTGTAC  CATGCATACT     300

CCTTTAAAAC  AAATAATGGT  GGTAACAGTA  AATCTGTCAT  CCCACCCACT  CTCATTGTAA     360

ATTTTGCAAG  TTCTCACTTG  AACTTCTTAA  TACTCCATCC  GTTTGCGTGT  GTTCTTTCAG     420

AATTTGCGTG  AGCACTTTTT  CTTCTATATA  ATCTGTCTAG  TCCATGAGCT  AAACCAACAT     480

CTCTCGCTGT  CTTGCCTTGC  ACTTCTGCAC  GATGATATCA  CTCCCATTAT  TGCTCTTCGT     540

CCTGTTGTTC  TCTGCGCTGC  TGCTCTGCCC  TTCAAGCAGT  GACGACGATG  GTGATGCTGC     600

CGGCGACGAA  CTCGCGCTGC  TCTCTTTCAA  GTCATCCCTG  CTATACCAGG  GGGGCCAGTC     660

GCTGGCATCT  TGGAACACGT  CCGGCCACGG  CCAGCACTGC  ACATGGGTGG  GTGTTGTGTG     720

CGGCCGCCGC  CGCCGCCGGC  ACCCACACAG  GGTGGTGAAG  CTGCTGCTGC  GCTCCTCCAA     780
```

```
CCTGTCCGGG ATCATCTCGC CGTCGCTCGG CAACCTGTCC TTCCTCAGGG AGCTGGACCT    840
CGGCGACAAC TACCTCTCCG GCGAGATACC ACCGGAGCTC AGCCGTCTCA GCAGGCTTCA    900
GCTGCTGGAG CTGAGCGATA ACTCCATCCA AGGGAGCATC CCCGCGGCCA TTGGAGCATG    960
CACCAAGTTG ACATCGCTAG ACCTCAGCCA CAACCAACTG CGAGGTATGA TCCCACGTGA   1020
GATTGGTGCC AGCTTGAAAC ATCTCTCGAA TTTGTACCTT TACAAAAATG GTTTGTCAGG   1080
AGAGATTCCA TCCGCTTTGG GCAATCTCAC TAGCCTCCAG GAGTTTGATT TGAGCTTCAA   1140
CAGATTATCA GGAGCTATAC CTTCATCACT GGGGCAGCTC AGCAGTCTAT TGACTATGAA   1200
TTTGGGACAG AACAATCTAA GTGGGATGAT CCCCAATTCT ATCTGGAACC TTTCGTCTCT   1260
AAGAGCGTTT AGTGTCAGAG AAAACAAGCT AGGTGGTATG ATCCCTACAA ATGCATTCAA   1320
AACCCTTCAC CTCCTCGAGG TGATAGATAT GGGCACTAAC CGTTTCCATG GCAAAATCCC   1380
TGCCTCAGTT GCTAATGCTT CTCATTTGAC AGTGATTCAG ATTTATGGCA ACTTGTTCAG   1440
TGGAATTATC ACCTCGGGGT TTGGAAGGTT AAGAAATCTC ACAGAACTGT ATCTCTGGAG   1500
AAATTTGTTT CAAACTAGAG AACAAGATGA TTGGGGGTTC ATTTCTGACC TAACAAATTG   1560
CTCCAAATTA CAAACATTGA ACTTGGGAGA AAATAACCTG GGGGAGTTC TTCCTAATTC    1620
GTTTTCCAAT CTTTCCACTT CGCTTAGTTT TCTTGCACTT GAATTGAATA AGATCACAGG   1680
AAGCATTCCG AAGGATATTG GCAATCTTAT TGGCTTACAA CATCTCTATC TCTGCAACAA   1740
CAATTTCAGA GGGTCTCTTC CATCATCGTT GGGCAGGCTT AAAAACTTAG GCATTCTACT   1800
CGCCTACGAA AACAACTTGA GCGGTTCGAT CCCGTTGGCC ATAGGAAATC TTACTGAACT   1860
TAATATCTTA CTGCTCGGCA CCAACAAATT CAGTGGTTGG ATACCATACA CACTCTCAAA   1920
CCTCACAAAC TTGTTGTCAT TAGGCCTTTC AACTAATAAC CTTAGTGGTC AATACCCAG    1980
TGAATTATTC AATATTCAAA CACTATCAAT AATGATCAAT GTATCAAAAA ATAACTTGGA   2040
GGGATCAATA CCACAAGAAA TAGGGCATCT CAAAAATCTA GTAGAATTTC ATGCAGAATC   2100
GAATAGATTA TCAGGTAAAA TCCCTAACAC GCTTGGTGAT TGCCAGCTCT TACGGTATCT   2160
TTATCTGCAA AATAATTTGT TATCTGGTAG CATCCCATCA GCCTTGGGTC AGCTGAAAGG   2220
TCTCGAAACT CTTGATCTCT CAAGCAACAA TTTGTCAGGC CAGATACCCA CATCCTTAGC   2280
AGATATTACT ATGCTTCATT CCTTGAACCT TTCTTTCAAC AGCTTTGTGG GGGAAGTGCC   2340
AACCATTGGT GCTTTCGCAG CTGCATCCGG GATCTCAATC CAAGGCAATG CCAAACTCTG   2400
TGGTGGAATA CCTGATCTAC ATCTGCCTCG ATGTTGTCCA TTACTAGAGA ACAGAAAACA   2460
TTTCCCAGTT CTACCTATTT CTGTTTCTCT GGCCGCAGCA CTGGCCATCC TCTCATCACT   2520
CTACTTGCTT ATAACCTGGC ACAAGAGAAC TAAAAAGGGA GCCCCTTCAA GAACTTCCAT   2580
GAAAGGCCAC CCATTGGTCT CTTATTCGCA GTTGGTAAAA GCAACAGATG GTTTCGCGCC   2640
GACCAATTTG TTGGGTTCTG GATCATTTGG CTCAGTATAC AAAGGAAAGC TTGAAAATCC   2700
TAAGGCGCTC AAGAGTTTCA CTGCCGAATG TGAAGCACTA CGAAATATGC GACATCGAAA   2760
TCTTGTCAAG ATAGTTACAA TTTGCTCGAG CATTGATAAC AGAGGGAACG ATTTCAAAGC   2820
AATTGTGTAT GACTTCATGC CCAACGGCAG TCTGGAAGAT TGGATACACC CTGAAACAAA   2880
TGATCAAGCA GACCAGAGGG ACTTGAATCT GCATCGAAGA GTGACCATAC TACTTGATGT   2940
TGCCTGCGCA CTGGACTATC TTCACCGCCA TGGCCCTGAA CCTGTTGTAC ACTGTGATAT   3000
TAAATCAAGC AATGTGCTGT TAGATTCTGA TATGGTAGCC CATGTTGGAG ATTTTGGGCT   3060
TGCAAGAATA CTTGTTGATG GGACCTCATT GATACAACAG TCAACAAGCT CGATGGGATT   3120
TATAGGGACA ATTGGCTATG CAGCACCAGG TCAGCAAGTC CTTCCAGTAT TTTGCATTTT   3180
```

```
CTGATCTCTA  GTGCTATATG  ATATAGTTTT  TACCTCTAGT  GAAACTGATG  GAGAATATAA    3240
GTAATTAATT  GAACTAATTA  AATTGCACAA  AAATAAGATT  ATTTGCCATA  TCTATTCAGA    3300
TGCTAAATAT  AGCTAGTTCA  TAGAGGTACA  GATTTTTTTA  TATAGGACTC  TAGAGCTACC    3360
ACACACTCAA  ATCAAATTAT  GGGTGTTTTC  TGCTCTACAC  TGCAATATGA  AATGATTATT    3420
ACTTCTACAT  GAACTGATGG  AGGAGTTTCA  GAAGGATCAA  ATTTGAGTAA  ATTTTTTCAA    3480
TTCTACATTT  AAGAAACACT  TTTTTTTCAT  ATGCTAGTTA  CATTTTTTTA  TTTCACGAGC    3540
TTACATTGAC  CATGAAAAAT  ACTTGGCACT  ACTTACTAAT  TCCCACATGG  AGGTAGTGAA    3600
AATAATATAG  ATACAAAAAC  GAAATATCCT  ATGTTGTGTG  ATATACTATA  ATCACAATGA    3660
ACACAAACAG  GATTCGTACA  AAAGTAATTA  GCCATCATAG  CAACTGATTG  CTTGGGGTAA    3720
CTGTATAGCA  CAATCATACC  AAATTTCTTT  AGATATGTAT  CTGTAAATTA  GATTCTTAAA    3780
GTTAAATATG  AAATTTCATT  GGTATTTATG  TTTCTTTATA  TAATAAAAAT  TAATCCAGCC    3840
TTTGCATCTA  TCATTTGTCC  AGACATCCTT  GTTATTTGTG  ATATTTAACA  CGTAAATTTA    3900
CATAATTATA  CATCCAAGTT  CTTTTTATTT  AACACTGTAA  ATTTCAAATC  GTACATGTTA    3960
TAAAGAATGT  ACTATATTTC  CTGCTCAAAC  AGAGTATGGC  GTTGGGCTCA  TTGCATCAAC    4020
GCATGGAGAT  ATTTACAGCT  ATGGAATTCT  AGTGCTGGAA  ATAGTAACCG  GGAAGCGGCC    4080
AACTGACAGT  ACATTCAGAC  CCGATTTGGG  CCTCCGTCAG  TACGTTGAAC  TGGGCCTACA    4140
TGGCAGAGTG  ACGGATGTTG  TTGACACGAA  GCTCATTTTG  GATTCTGAGA  ACTGGCTGAA    4200
CAGTACAAAT  AATTCTCCAT  GTAGAAGAAT  CACTGAATGC  ATTGTTTGGC  TGCTTACACT    4260
TGGGTTGTCT  TGCTCTCAGG  AATTGCCATC  GAGTAGAACG  CCAACCGGAG  ATATCATCGA    4320
CGAACTGAAT  GCCATCAAAC  AGAATCTCTC  CGGATTGTTT  CCAGTGTGTG  AAGGTGGGAG    4380
CCTTGAATTC  TGATGTTATG  TCTCGTAATG  TTTTATTGCC  ACACTTCAGA  TCGACTTCTG    4440
CAGTGGTATC  TACCACACGA  TCACTAAAGT  CACCGTGGCT  ATTTCCTGAT  CCAGCATATC    4500
TGATCATGCA  TGTTCTGTGT  TGTATACCTG  TATTTTACTC  TGAATTGCCA  CACCGCAACC    4560
CTGCCTCTGT  TTGTTTGGTA  TACAAAGAT   AGTGATGAGT  TTATTGTTTT  AGGGGCTTCC    4620
TAGTTGGCGC  GTGTGCATGC  CGGCATGCAC  GCAGCCCGAG  GGTGGGTTTC  TTTTTTTTCC    4680
ATTGTTATTC  CGTTGCTTTT  TTTCACCACG  GTAGATTTTT  TTTTCCGGAT  TTCCATTTTT    4740
TCCGTTGTTT  TTCTCTATCG  CTTATGTTGG  CGGATTTTTT  TCCGTGGTTT  TCTTTCCGAA    4800
GACGAGTATA  TCTAACGTAA  CTAACATGTT  ACTTTTAGAT  AACGATGGTT  ATTAAGATAA    4860
GATTTTTCTC  TGGAAGATTT  TTGTAAGTAA  CAGATTGAAA  ACAAATCTAT  ACGTGAGGTC    4920
AAATTTTGAA  AACTTTCAAT  CTAGATTTAA  AAGCTTTTCA  ACTCAAAATT  TGAATTTTTG    4980
AAGTGAAAAT  TTGAATACTT  TCAAAAATTA  CTAGTAATCG  ACAAAAAAAA  TATGGAAATG    5040
GAAACGGAAA  TAGTTTTGCT  GTTATACCGA  TCGTTTCCAT  ATTACCGTA   TTCTTATAGA    5100
AATTACCGTT  TCTTATAATA  TGGTAATTAC  CGTATTTCTA  AATATGTTGA  TATTTATAGG    5160
GCATGTCTCT  ACTTGACTCA  CAGTTTAGAG  ATTGATTGAC  TATTTAATCA  AATCCCTAAC    5220
TTGATTGCAT  GGCTAAAATG  GAGTTGATTT  CTAATTTATA  TAGTATAGCT  TAAATTTATT    5280
TGTAAATATA  ACATACTTAT  GTAAAGTTAA  ATATATGTTT  TCTATAGTTT  AATGTTTCTG    5340
TATTTGTTAC  CNGGTTTTCN  GATCTGTACC  GACATATTTC  CATCAGTATT  ATTCCATTTC    5400
CGTTTTCCGA  TATTTCCGAT  ATCGTTTTCG  TTTCCGACTT  TACCGTTTTC  GATTTCATTT    5460
CCGAGAAAAA  TATGATTATG  GAAATGGTCG  AGGCTGTTTT  CCGATCGTTT  CCGACCGTTT    5520
TCATCCCTAC  CCGTAGTAAT  AATATATAAC  ATTTTATCTC  TAATCTTTCT  CTCTCTCATA    5580
```

```
TCAATGAATA   ATCGCTAAGA   GACTGCTATT   AACAAGGCTT   ATATATATAT   ATGCCGTCGA        5640

TCAGTCATTT   TGAAACGGCC   CACTTCTTTT   CCATCTATAT   GCATTCATGA   AATACATGGT        5700

ATATCCATC    GATCGGACAT   CACCTGTTAG   CGCGTACGCC   ATCGTCGTCA   TCAACCTAGC        5760

TAGGGCAAAC   GCACCTTGCT   GAGCTCCGAT   CCTCCGATCG   CCACCATCAC   CAATGAACAA        5820

GCTGCTGGCG   GCCTCTCGGT   GGCCTGAGGT   TGCTCAACCG   AGAAGAACAT   CCGTTCCGAT        5880

GCTTCTCCTC   CTCCATCGAT   CTCGTCTTCC   CAGGTCGCCG   CCGCCGCCAC   ATGGCAACCA        5940

CCGTGACCCA   CCCGCCGCCG   ACGGAATCCG   CTGGTTCGAC   GGCGGCGGCC   GC                5992
```

( 2 ) INFORMATION FOR SEQ ID NO:4:

( i ) SEQUENCE CHARACTERISTICS:
        ( A ) LENGTH: 1012 amino acids
        ( B ) TYPE: amino acid
        ( C ) STRANDEDNESS:
        ( D ) TOPOLOGY: linear ( i i ) MOLECULE TYPE: protein ( i x ) FEATURE:
        ( A ) NAME/KEY: Protein
        ( B ) LOCATION: 1..1012
        ( D ) OTHER INFORMATION: /note= "Xa21 Xanthomonas spp.
            disease resistance polypeptide RRK-B
            from rice (Oryza sativa)"

( x i ) SEQUENCE DESCRIPTION: SEQ ID NO:4:

```
Met  Ile  Ser  Leu  Pro  Leu  Leu  Leu  Phe  Val  Leu  Leu  Phe  Ser  Ala  Leu
 1              5                        10                       15

Leu  Leu  Cys  Pro  Ser  Ser  Ser  Asp  Asp  Asp  Gly  Asp  Ala  Ala  Gly  Asp
              20                        25                       30

Glu  Leu  Ala  Leu  Leu  Ser  Phe  Lys  Ser  Ser  Leu  Leu  Tyr  Gln  Gly  Gly
         35                        40                       45

Gln  Ser  Leu  Ala  Ser  Trp  Asn  Thr  Ser  Gly  His  Gly  Gln  His  Cys  Thr
     50                        55                       60

Trp  Val  Gly  Val  Val  Cys  Gly  Arg  Arg  Arg  Arg  His  Pro  His  Arg
65                        70                       75                       80

Val  Val  Lys  Leu  Leu  Leu  Arg  Ser  Ser  Asn  Leu  Ser  Gly  Ile  Ile  Ser
                    85                        90                       95

Pro  Ser  Leu  Gly  Asn  Leu  Ser  Phe  Leu  Arg  Glu  Leu  Asp  Leu  Gly  Asp
                   100                       105                      110

Asn  Tyr  Leu  Ser  Gly  Glu  Ile  Pro  Pro  Glu  Leu  Ser  Arg  Leu  Ser  Arg
          115                       120                      125

Leu  Gln  Leu  Leu  Glu  Leu  Ser  Asp  Asn  Ser  Ile  Gln  Gly  Ser  Ile  Pro
     130                       135                      140

Ala  Ala  Ile  Gly  Ala  Cys  Thr  Lys  Leu  Thr  Ser  Leu  Asp  Leu  Ser  His
145                       150                      155                      160

Asn  Gln  Leu  Arg  Gly  Met  Ile  Pro  Arg  Glu  Ile  Gly  Ala  Ser  Leu  Lys
                   165                       170                      175

His  Leu  Ser  Asn  Leu  Tyr  Leu  Tyr  Lys  Asn  Gly  Leu  Ser  Gly  Glu  Ile
               180                       185                      190

Pro  Ser  Ala  Leu  Gly  Asn  Leu  Thr  Ser  Leu  Gln  Glu  Phe  Asp  Leu  Ser
          195                       200                      205

Phe  Asn  Arg  Leu  Ser  Gly  Ala  Ile  Pro  Ser  Ser  Leu  Gly  Gln  Leu  Ser
     210                       215                      220

Ser  Leu  Leu  Thr  Met  Asn  Leu  Gly  Gln  Asn  Asn  Leu  Ser  Gly  Met  Ile
225                       230                      235                      240
```

|     |     |     |     |     |     |     |     |     |     |     |     |     |     |     |
|---|---|---|---|---|---|---|---|---|---|---|---|---|---|---|
| Pro | Asn | Ser | Ile | Trp<br>245 | Asn | Leu | Ser | Ser<br>250 | Leu | Arg | Ala | Phe | Ser<br>255 | Val | Arg |
| Glu | Asn | Lys | Leu<br>260 | Gly | Gly | Met | Ile | Pro<br>265 | Thr | Asn | Ala | Phe | Lys<br>270 | Thr | Leu |
| His | Leu | Leu<br>275 | Glu | Val | Ile | Asp | Met<br>280 | Gly | Thr | Asn | Arg | Phe<br>285 | His | Gly | Lys |
| Ile | Pro | Ala<br>290 | Ser | Val | Ala | Asn | Ala<br>295 | Ser | His | Leu | Thr | Val<br>300 | Ile | Gln | Ile |
| Tyr<br>305 | Gly | Asn | Leu | Phe | Ser<br>310 | Gly | Ile | Ile | Thr | Ser<br>315 | Gly | Phe | Gly | Arg | Leu<br>320 |
| Arg | Asn | Leu | Thr | Glu<br>325 | Leu | Tyr | Leu | Trp | Arg<br>330 | Asn | Leu | Phe | Gln | Thr<br>335 | Arg |
| Glu | Gln | Asp | Asp<br>340 | Trp | Gly | Phe | Ile | Ser<br>345 | Asp | Leu | Thr | Asn | Cys<br>350 | Ser | Lys |
| Leu | Gln | Thr<br>355 | Leu | Asn | Leu | Gly | Glu<br>360 | Asn | Asn | Leu | Gly | Gly<br>365 | Val | Leu | Pro |
| Asn | Ser | Phe<br>370 | Ser | Asn | Leu | Ser<br>375 | Thr | Ser | Leu | Ser | Phe<br>380 | Leu | Ala | Leu | Glu |
| Leu<br>385 | Asn | Lys | Ile | Thr | Gly<br>390 | Ser | Ile | Pro | Lys | Asp<br>395 | Ile | Gly | Asn | Leu | Ile<br>400 |
| Gly | Leu | Gln | His | Leu<br>405 | Tyr | Leu | Cys | Asn | Asn<br>410 | Phe | Arg | Gly | Ser<br>415 | Leu |
| Pro | Ser | Ser | Leu<br>420 | Gly | Arg | Leu | Lys | Asn<br>425 | Leu | Gly | Ile | Leu<br>430 | Leu | Ala | Tyr |
| Glu | Asn | Asn<br>435 | Leu | Ser | Gly | Ser | Ile<br>440 | Pro | Leu | Ala | Ile | Gly<br>445 | Asn | Leu | Thr |
| Glu | Leu | Asn<br>450 | Ile | Leu | Leu | Leu<br>455 | Gly | Thr | Asn | Lys | Phe<br>460 | Ser | Gly | Trp | Ile |
| Pro<br>465 | Tyr | Thr | Leu | Ser | Asn<br>470 | Leu | Thr | Asn | Leu | Leu<br>475 | Ser | Leu | Gly | Leu | Ser<br>480 |
| Thr | Asn | Asn | Leu | Ser<br>485 | Gly | Pro | Ile | Pro | Ser<br>490 | Glu | Leu | Phe | Asn | Ile<br>495 | Gln |
| Thr | Leu | Ser | Ile<br>500 | Met | Ile | Asn | Val | Ser<br>505 | Lys | Asn | Asn | Leu | Glu<br>510 | Gly | Ser |
| Ile | Pro | Gln<br>515 | Glu | Ile | Gly | His | Leu<br>520 | Lys | Asn | Leu | Val | Glu<br>525 | Phe | His | Ala |
| Glu | Ser<br>530 | Asn | Arg | Leu | Ser | Gly<br>535 | Lys | Ile | Pro | Asn | Thr<br>540 | Leu | Gly | Asp | Cys |
| Gln<br>545 | Leu | Leu | Arg | Tyr | Leu<br>550 | Tyr | Leu | Gln | Asn | Asn<br>555 | Leu | Leu | Ser | Gly | Ser<br>560 |
| Ile | Pro | Ser | Ala | Leu<br>565 | Gly | Gln | Leu | Lys | Gly<br>570 | Leu | Glu | Thr | Leu | Asp<br>575 | Leu |
| Ser | Ser | Asn | Asn<br>580 | Leu | Ser | Gly | Gln | Ile<br>585 | Pro | Thr | Ser | Leu | Ala<br>590 | Asp | Ile |
| Thr | Met | Leu<br>595 | His | Ser | Leu | Asn | Leu<br>600 | Ser | Phe | Asn | Ser | Phe<br>605 | Val | Gly | Glu |
| Val | Pro<br>610 | Thr | Ile | Gly | Ala | Phe<br>615 | Ala | Ala | Ala | Ser | Gly<br>620 | Ile | Ser | Ile | Gln |
| Gly<br>625 | Asn | Ala | Lys | Leu | Cys<br>630 | Gly | Gly | Ile | Pro | Asp<br>635 | Leu | His | Leu | Pro | Arg<br>640 |
| Cys | Cys | Pro | Leu | Leu<br>645 | Glu | Asn | Arg | Lys | His<br>650 | Phe | Pro | Val | Leu | Pro<br>655 | Ile |
| Ser | Val | Ser | Leu<br>660 | Ala | Ala | Ala | Leu | Ala<br>665 | Ile | Leu | Ser | Ser | Leu<br>670 | Tyr | Leu |

| | | | | | | | | | | | | | | |
|---|---|---|---|---|---|---|---|---|---|---|---|---|---|---|
| Leu | Ile | Thr 675 | Trp | His | Lys | Arg | Thr 680 | Lys | Lys | Gly | Ala | Pro 685 | Ser | Arg | Thr |
| Ser | Met 690 | Lys | Gly | His | Pro | Leu 695 | Val | Ser | Tyr | Ser | Gln 700 | Leu | Val | Lys | Ala |
| Thr 705 | Asp | Gly | Phe | Ala | Pro 710 | Thr | Asn | Leu | Leu | Gly 715 | Ser | Gly | Ser | Phe | Gly 720 |
| Ser | Val | Tyr | Lys | Gly 725 | Lys | Leu | Glu | Asn | Pro 730 | Lys | Ala | Leu | Lys | Ser 735 | Phe |
| Thr | Ala | Glu | Cys 740 | Glu | Ala | Leu | Arg | Asn 745 | Met | Arg | His | Arg | Asn 750 | Leu | Val |
| Lys | Ile | Val 755 | Thr | Ile | Cys | Ser | Ser 760 | Ile | Asp | Asn | Arg | Gly 765 | Asn | Asp | Phe |
| Lys | Ala 770 | Ile | Val | Tyr | Asp | Phe 775 | Met | Pro | Asn | Gly | Ser 780 | Leu | Glu | Asp | Trp |
| Ile 785 | His | Pro | Glu | Thr | Asn 790 | Asp | Gln | Ala | Asp | Gln 795 | Arg | Asp | Leu | Asn | Leu 800 |
| His | Arg | Arg | Val | Thr 805 | Ile | Leu | Leu | Asp | Val 810 | Ala | Cys | Ala | Leu | Asp 815 | Tyr |
| Leu | His | Arg | His 820 | Gly | Pro | Glu | Pro | Val 825 | Val | His | Cys | Asp | Ile 830 | Lys | Ser |
| Ser | Asn | Val 835 | Leu | Leu | Asp | Ser | Asp 840 | Met | Val | Ala | His | Val 845 | Gly | Asp | Phe |
| Gly | Leu 850 | Ala | Arg | Ile | Leu | Val 855 | Asp | Gly | Thr | Ser | Leu 860 | Ile | Gln | Gln | Ser |
| Thr 865 | Ser | Ser | Met | Gly | Phe 870 | Ile | Gly | Thr | Ile | Gly 875 | Tyr | Ala | Ala | Pro | Glu 880 |
| Tyr | Gly | Val | Gly | Leu 885 | Ile | Ala | Ser | Thr | His 890 | Gly | Asp | Ile | Tyr | Ser 895 | Tyr |
| Gly | Ile | Leu | Val 900 | Leu | Glu | Ile | Val | Thr 905 | Gly | Lys | Arg | Pro | Thr 910 | Asp | Ser |
| Thr | Phe | Arg 915 | Pro | Asp | Leu | Gly | Leu 920 | Arg | Gln | Tyr | Val | Glu 925 | Leu | Gly | Leu |
| His | Gly 930 | Arg | Val | Thr | Asp | Val 935 | Val | Asp | Thr | Lys | Leu 940 | Ile | Leu | Asp | Ser |
| Glu 945 | Asn | Trp | Leu | Asn | Ser 950 | Thr | Asn | Asn | Ser | Pro 955 | Cys | Arg | Arg | Ile | Thr 960 |
| Glu | Cys | Ile | Val | Trp 965 | Leu | Leu | Thr | Leu | Gly 970 | Leu | Ser | Cys | Ser | Gln 975 | Glu |
| Leu | Pro | Ser | Ser 980 | Arg | Thr | Pro | Thr | Gly 985 | Asp | Ile | Ile | Asp | Glu 990 | Leu | Asn |
| Ala | Ile | Lys 995 | Gln | Asn | Leu | Ser | Gly 1000 | Leu | Phe | Pro | Val | Cys 1005 | Glu | Gly | Gly |
| Ser | Leu | Glu 1010 | Phe | | | | | | | | | | | | |

( 2 ) INFORMATION FOR SEQ ID NO:5:

( i ) SEQUENCE CHARACTERISTICS:
    ( A ) LENGTH: 24 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Modified-site (B) LOCATION: one-of(3, 5, 6, 8, 9, 11, 12, 14, 16, 17, 19, 23
(D) OTHER INFORMATION: /note= "Xaa = non-conserved amino
acid residue in rice (Oryza sativa)
protein RRK- F (Xa21-type disease
resistance) leucine-rich repeat (LRR)"

(xi) SEQUENCE DESCRIPTION: SEQ ID NO:5:

```
Pro Ser Xaa Leu Xaa Xaa Leu Xaa Xaa Leu Xaa Xaa Leu Xaa Leu Xaa
 1               5                   10                  15
Xaa Asn Xaa Leu Ser Gly Xaa Ile
            20
```

(2) INFORMATION FOR SEQ ID NO:6:

(i) SEQUENCE CHARACTERISTICS:
      (A) LENGTH: 23 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Modified-site
      (B) LOCATION: one-of(2, 3, 5, 6, 8, 9, 11, 12, 14, 16, 17, 19,
           21, 22)
      (D) OTHER INFORMATION: /note= "Xaa = non-conserved amino
acid residue in yeast protein adcyc
leucine- rich repeat (LRR)"

(xi) SEQUENCE DESCRIPTION: SEQ ID NO:6:

```
Pro Xaa Xaa Leu Xaa Xaa Leu Xaa Xaa Leu Xaa Xaa Leu Xaa Leu Xaa
 1               5                   10                  15
Xaa Asn Xaa Leu Xaa Xaa Leu
            20
```

(2) INFORMATION FOR SEQ ID NO:7:

(i) SEQUENCE CHARACTERISTICS:
      (A) LENGTH: 24 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Modified-site
      (B) LOCATION: one-of(2, 3, 6, 8, 9, 12, 13, 15, 17, 18, 20,
           22, 23)
      (D) OTHER INFORMATION: /note= "Xaa = non-conserved amino
acid residue in fruit fly (Drosophila)
protein TO11 leucine-rich repeat (LRR)"

(xi) SEQUENCE DESCRIPTION: SEQ ID NO:7:

```
Pro Xaa Xaa Leu Phe Xaa His Xaa Xaa Asn Leu Xaa Xaa Leu Xaa Leu
 1               5                   10                  15
Xaa Xaa Asn Xaa Leu Xaa Xaa Leu
            20
```

(2) INFORMATION FOR SEQ ID NO:8:

(i) SEQUENCE CHARACTERISTICS:
      (A) LENGTH: 24 amino acids
      (B) TYPE: amino acid
      (C) STRANDEDNESS:
      (D) TOPOLOGY: linear (ii) MOLECULE TYPE: peptide (ix) FEATURE:

( A ) NAME/KEY: Modified-site
( B ) LOCATION: one-of(2, 3, 5, 6, 8, 9, 11, 12, 14, 17, 19, 23)
( D ) OTHER INFORMATION: /note= "Xaa = non-conserved amino
acid residue in Arabidopsis protein
RLK5 leucine- rich repeat (LRR)"

( x i ) SEQUENCE DESCRIPTION: SEQ ID NO:8:

Pro  Xaa  Xaa  Leu  Xaa  Xaa  Leu  Xaa  Xaa  Leu  Xaa  Xaa  Leu  Xaa  Leu  Ser
1                   5                         10                        15

Xaa  Asn  Xaa  Leu  Ser  Gly  Xaa  Ile
                 20

( 2 ) INFORMATION FOR SEQ ID NO:9:

( i ) SEQUENCE CHARACTERISTICS:
( A ) LENGTH: 24 amino acids
( B ) TYPE: amino acid
( C ) STRANDEDNESS:
( D ) TOPOLOGY: linear ( i i ) MOLECULE TYPE: peptide ( i x ) FEATURE:
( A ) NAME/KEY: Modified-site
( B ) LOCATION: one-of(2, 3, 5, 6, 8, 9, 11, 14, 17, 19, 21, 23)
( D ) OTHER INFORMATION: /note= "Xaa = non-conserved amino
acid residue in snapdragon protein Fil2
leucine- rich repeat (LRR)"

( x i ) SEQUENCE DESCRIPTION: SEQ ID NO:9:

Pro  Xaa  Xaa  Leu  Xaa  Xaa  Leu  Xaa  Xaa  Leu  Xaa  Ser  Leu  Xaa  Leu  Ser
1                   5                         10                        15

Xaa  Asn  Xaa  Leu  Xaa  Gly  Xaa  Ile
                 20

( 2 ) INFORMATION FOR SEQ ID NO:10:

( i ) SEQUENCE CHARACTERISTICS:
( A ) LENGTH: 24 amino acids
( B ) TYPE: amino acid
( C ) STRANDEDNESS:
( D ) TOPOLOGY: linear ( i i ) MOLECULE TYPE: peptide ( i x ) FEATURE:
( A ) NAME/KEY: Modified-site
( B ) LOCATION: one-of(2, 3, 4, 5, 6, 8, 9, 11, 12, 14, 17, 19,
     21, 23)
( D ) OTHER INFORMATION: /note= "Xaa = non-conserved amino
acid residue in tomato protein PGIP
leucine- rich repeat (LRR)"

( x i ) SEQUENCE DESCRIPTION: SEQ ID NO:10:

Pro  Xaa  Xaa  Xaa  Xaa  Xaa  Leu  Xaa  Xaa  Leu  Xaa  Xaa  Leu  Xaa  Leu  Ser
1                   5                         10                        15

Xaa  Asn  Xaa  Leu  Xaa  Gly  Xaa  Ile
                 20

( 2 ) INFORMATION FOR SEQ ID NO:11:

( i ) SEQUENCE CHARACTERISTICS:
( A ) LENGTH: 24 amino acids
( B ) TYPE: amino acid
( C ) STRANDEDNESS:
( D ) TOPOLOGY: linear ( i i ) MOLECULE TYPE: peptide ( i x ) FEATURE:
( A ) NAME/KEY: Modified-site ( B ) LOCATION: one-of(3, 5, 6, 8, 9, 11, 12, 14, 17, 18, 19, 21, 23)
( D ) OTHER INFORMATION: /note= "Xaa = non-conserved amino acid resudue in tomato protein Cf-9 leucine- rich repeat (LRR)"

( x i ) SEQUENCE DESCRIPTION: SEQ ID NO:11:

Pro Ser Xaa Leu Xaa Xaa Leu Xaa Xaa Leu Xaa Xaa Leu Xaa Leu Ser
1               5                   10                  15

Xaa Xaa Xaa Leu Xaa Gly Xaa Ile
            20

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:12:

Ser Trp Asn Thr Ser
1               5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:13:

Asp Ile Lys Ser Ser Asn
1               5

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:14:

Gly Thr Ile Gly Tyr Ala Ala Pro Glu
1               5

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Xaa = asparagine or glutamine"

( i x ) FEATURE:

-continued (A) NAME/KEY: Modified-site
        (B) LOCATION: 2
        (D) OTHER INFORMATION: /note= "Xaa = any amino acid"

(ix) FEATURE:
        (A) NAME/KEY: Modified-site
        (B) LOCATION: 3
        (D) OTHER INFORMATION: /note= "Xaa = leucine or valine"

(ix) FEATURE:
        (A) NAME/KEY: Modified-site
        (B) LOCATION: 5
        (D) OTHER INFORMATION: /note= "Xaa = glycine or serine"

(ix) FEATURE:
        (A) NAME/KEY: Modified-site
        (B) LOCATION: 6
        (D) OTHER INFORMATION: /note= "Xaa = leucine or alanine"

(ix) FEATURE:
        (A) NAME/KEY: Modified-site
        (B) LOCATION: 7
        (D) OTHER INFORMATION: /note= "Xaa = phenylalanine or valine"

(ix) FEATURE:
        (A) NAME/KEY: Modified-site
        (B) LOCATION: 8
        (D) OTHER INFORMATION: /note= "Xaa = proline or glutamic acid"

(xi) SEQUENCE DESCRIPTION: SEQ ID NO:15:

Xaa  Xaa  Xaa  Ser  Xaa  Xaa  Xaa  Xaa
    1              5